US007361459B2

(12) United States Patent
Summers et al.

(10) Patent No.: US 7,361,459 B2
(45) Date of Patent: Apr. 22, 2008

(54) ANTIVIRAL INHIBITION OF CAPSID PROTEINS

(75) Inventors: Michael F. Summers, Ellicott City, MD (US); Chun Tang, Baltimore, MD (US); Mingjun Huang, Potomac, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 723 days.

(21) Appl. No.: 10/420,438

(22) Filed: Apr. 22, 2003

(65) Prior Publication Data

US 2003/0228573 A1 Dec. 11, 2003

Related U.S. Application Data

(60) Provisional application No. 60/404,043, filed on Aug. 16, 2002, provisional application No. 60/375,852, filed on Apr. 25, 2002, provisional application No. 60/374,557, filed on Apr. 22, 2002.

(51) Int. Cl.
*C12Q 1/70* (2006.01)
*A61K 39/21* (2006.01)

(52) U.S. Cl. ........................ 435/5; 424/188.1
(58) Field of Classification Search ............... None
See application file for complete search history.

(56) References Cited

U.S. PATENT DOCUMENTS

| | | | |
|---|---|---|---|
| 5,656,627 A | 8/1997 | Bemis et al. | 514/221 |
| 5,716,929 A | 2/1998 | Bemis et al. | 514/18 |
| 5,756,466 A | 5/1998 | Bemis et al. | 514/18 |
| 5,843,904 A | 12/1998 | Bemis et al. | 514/18 |
| 6,008,217 A | 12/1999 | Batchelor et al. | 514/221 |
| 6,025,147 A | 2/2000 | Bemis et al. | 435/7.6 |
| 6,103,711 A | 8/2000 | Bemis et al. | 514/183 |
| 6,162,790 A | 12/2000 | Bemis et al. | 514/18 |
| 2001/0036627 A1 | 11/2001 | Prevelige | 435/5 |
| 2002/0094523 A1 | 7/2002 | Sakalian et al. | 435/5 |
| 2003/0104577 A1 | 6/2003 | Lingappa et al. | 435/69.3 |

OTHER PUBLICATIONS

Fitzon, Leschonsky, Bieler, Paulus, Schroder, Wolf and Wagner (2000), Virology, 268, 294-307.*
Dorfman and Gottlinger (1996) Journal of Virology. (70)9:5751-5757.*
von Schwedler et al (1998). EMBO Journal. 17(6): 1555-1568.*
Gamble et al (1996). Cell. 87: 1285-1294.*
Coffin, J., "HIV Population Dynamic In vivo: Implications for Genetic Variation ,Pathogenesis and Therapy, Science" 267:483-89 (1995).
Forshey, et al., "Formation of a Human Immunodeficiency Virus Type 1 Core of Optimal Stability is Crucial for Viral Replication", J. virol. 76:5667-5677 (2002).
Gitti, et al., "Structure of the amino-terminal core domain of the HIV-1 capsid protein", Science, 273:231-35 (1996).
Gross, et al., "N-terminal extension of human immunodeficiency virus capsid protein converts the in vitro assembly phenotype from tubular to spherical particles", J. Virol., 72: 4798-4810 (1998).

Huang, et al., "p6Gag is required for particle production from full length human immunodeficiency virus type 1 molecular clones expressing protease", J. Virol., 96:6810-18 (1995).
Kimpton, et al., "Detection of a replication-competent and pseudotyped HIV with a sensitive cell line on the basis of activation of an integrated B-galactosidase gene", J. Virol. 66: 2232-39 (1992).
Kuritzkes, D. R., "Clinical significance of drug resistance in HIV-1 infection" AIDS 10:S27-33 (1996).
Mansky, et al., "Combination of drugs and drug resistant reverse transcriptase results in a multiplicative increase of human immunodeficiency virus type 1 mutant frequencies", J. Virol., 76:9253-59 (2002).
O'Brien et al. "HIV causes AIDS: Koch's postulates fulfilled", Curr Opin Immunol 8:613 (1996).
Pillay, et al., "Incidence and impact of resistance against approved antiretroviral drugs", Rev Med Virol, 10:231-53 (2000).
Reicin, et al., "The role of Gag in human immunodeficiency virus type 1 virion morphogenesis and early steps of the viral life cycle"., J. Virol., 70:8645-52 (1996).
Richman, D.D., HIV chemotherapy, Nature 410:995-1001 (2001).
Smith, et al., "The site of attachment in human rhinovirus 14 for antiviral agents that inhibit uncoating", Science, 233: 1286-93 (1986).
Tang, et al. "Antiviral Inhibition of the HIV-1 Capsid Protein", J. Mol. Biol 327:1013-1020 (2003).
Tang, et al., "Human immunodeficiency virus type 1 N-terminal capsid mutants that exhibit aberrant core morphology are blocked in initiation of reverse transcription in infected cells", J. Virol. 75:9357-66 (2001).
Von Schwedler, et al., "Proteolytic refolding of the HIV-1 capsid protein amino-terminus facilitates viral core assembly", EMBO J., 17:1555-68 (1998).
Billich et al., "Mode of Action of SDZ NIM 811, a Nonimmunosuppressive Cyclosporin A Analog with Activity against Human Immunodeficiency Virus (HIV) Type 1: Interference with HIV Protein-Cyclophilin A Interactions" Journal of Virology, 69:4 (1995) pp. 2451-2461.
Campos-Olivas et al., "Backbone Dynamics of the N-Terminal Domain of the HIV-1 Capsid Protein and Comparison with the G94D Mutant Conferring Cyclosporin Resistance/Dependence" Biochemistry 38 (1999) pp. 10262-10271.
Chatterji et al., "Naturally Occurring Capsid Substitutions Render HIV-1 Cyclophilin A Independent in Human Cells and TRIM-Cyclophilin-resistant in Owl Monkey Cells" J. Biol. Chem. 280: 48 (2005) pp. 40293-40300.
Thali et al., "Functional Association Cyclophilin A with HIV-1 Virions" Nature 372 (1994) pp. 363-365.
Turner et al., "Structural Biology of HIV" J. Mol. Biol. 285 (1999) pp. 1-32.

* cited by examiner

*Primary Examiner*—Bruce R. Campell
*Assistant Examiner*—Michelle Horning
(74) *Attorney, Agent, or Firm*—Wilmer Cutler Pickering Hale & Dorr LLP

(57) ABSTRACT

Methods for evaluating the antiviral activity of test compounds are provided. Further aspects of the methods involve the retroviral capsid protein of HIV-1. In another aspect, methods of reducing mortality associated with AIDS with a compound that binds to the apical cleft near the C-terminal end of the N-terminal domain of the HIV-1 capsid protein are provided. Derivatives of CAP-1, CAP-2, CAP-3, CAP-4, CAP-5, CAP-6 and CAP-7 are described that bind to the apical cleft of the N-terminal domain of the HIV-1 capsid protein and inhibit proper assembly of the core particle.

7 Claims, 19 Drawing Sheets

CAP 1 docked in the structure of the capsid protein

Illustration of the short-range interactions involved in the binding of CAP 1 to the capsid protein binding site

Table 1. Structural statistics for 20 lowest energy Gag$^{283}$ conformers

NMR derived restraints[1]

| | |
|---|---|
| Interproton restraints | 1737 |
|    Interresidue restraints | 117 |
|    Sequential restraints | 447 |
|    Medium range restraints ($1 < |j\text{-}i| < 5$) | 829 |
|    Long range restraints ($|j\text{-}i| > 4$) | 344 |
|    Hydrogen bond restraints | 308 |
| Dihedral angle restraints ($\phi, \psi$)[2] | 332 |
| Total restraints | 2376 |

Residual restraint violations (Å$^2$)

| | |
|---|---|
| DYANA target function | 1.50±0.24 |
| Maximum violations | |
|    Upper limits | 0.21±0.03 |
|    Lower limits | 0.07±0.02 |
|    Van de Walls | 0.28±0.01 |
|    Torsion angles (radian) | 0.04±0.01 |

Average RMS deviations (Å)

| | Backbone heavy atoms | All heavy atoms |
|---|---|---|
| MA helices | 0.41±0.09 | 1.26±0.11 |
| CA helices | 0.72±0.14 | 1.47±0.1 |
| All helices | 22.33±7.02 | 22.77±7.06 |

RMS deviations from mature proteins[3], (Å)

| | NMR structures | X-ray structures |
|---|---|---|
| MA helices | 1.27 ± 0.05 | 1.14 ± 0.09 |
| | | (0.90 ± 0.09)[4] |
| CA$^N$ helices | 1.32 ± 0.13 | 1.07 ± 0.09 |
| | (1.13 ± 0.11)[5] | |

Ramachandran analysis[6]

| | |
|---|---|
| Residues in most favored regions | 87.7% |
| Residues in additional allowed regions | 9.1% |
| Residues in generously allowed regions | 2.3% |

1. residues 6-122, 144-176 and 179-278 are restrained.
2. Derived with TALOS and from couplings measured in HNHA data.
3. PDB accession numbers: mature MA NMR, 2HMX[22]; mature MA X-ray, 1HIW[23]; mature CA$^N$ NMR, 1GWP (this work and ref. [4]); mature CA$^N$ X-ray, 1AK4[5].
4. Residues Pro 66-Gly 71 were eliminated from the fitting; see text.
5. Residues Thr 242-Thr 251 were eliminated from the fitting; see text.
6. Only non-Gly and non-Pro were assessed with PROCHECK-NMR.

Figure 7

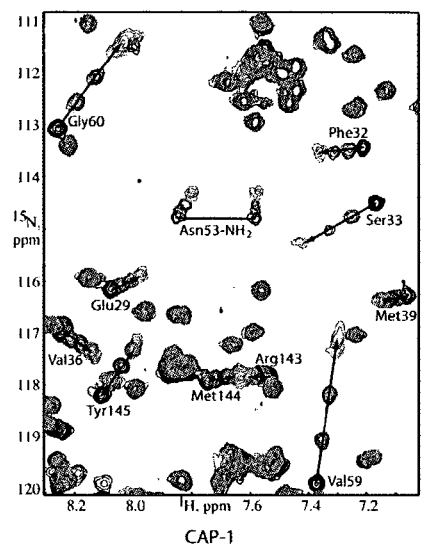
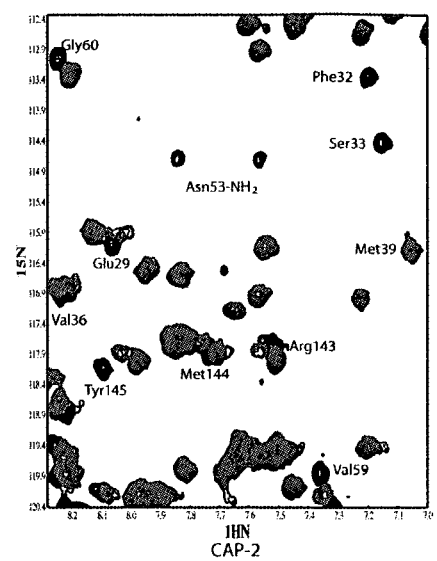
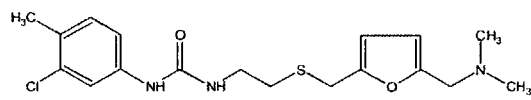
CAP-1
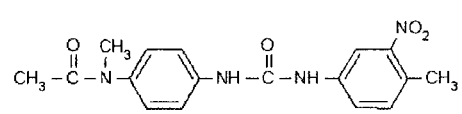
CAP-2
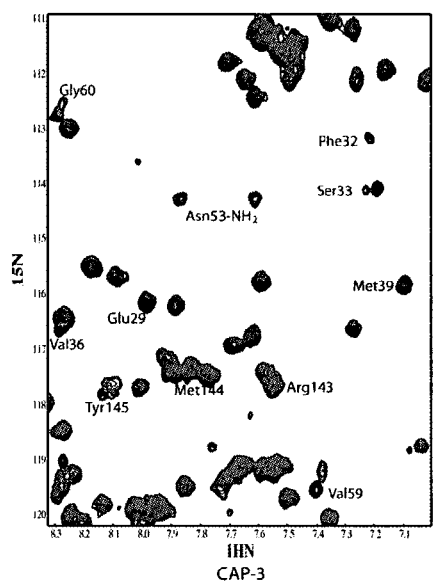
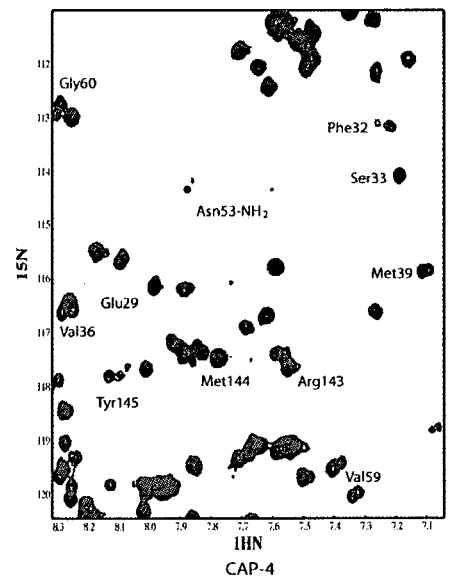
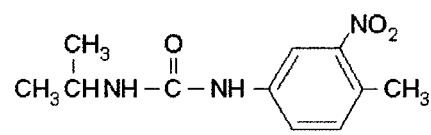
CAP-3
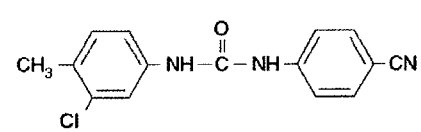
CAP-4
Figure 13

CAP-5 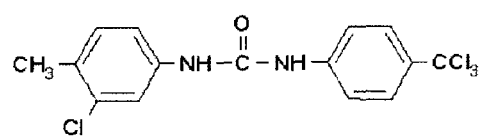 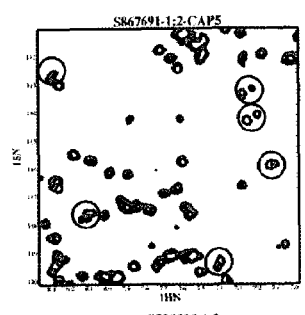
CAP-6 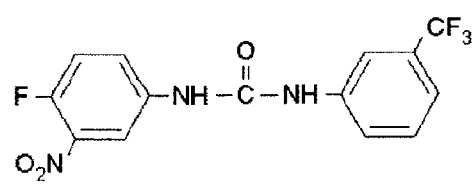 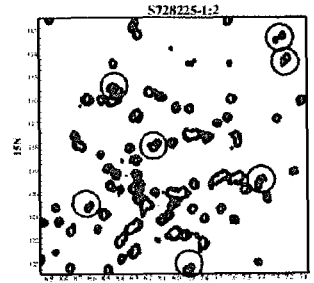
CAP-7 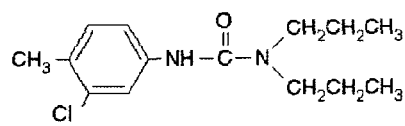 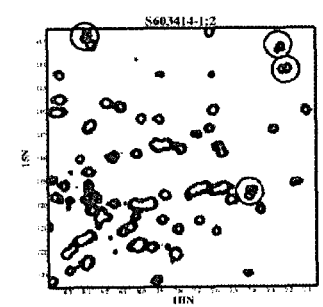
~ No Binding 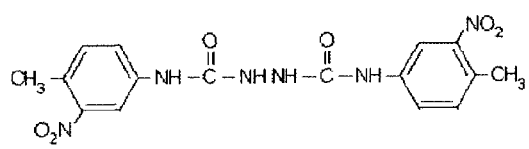 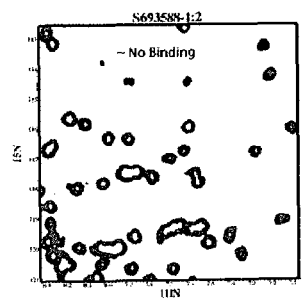
~ No Binding 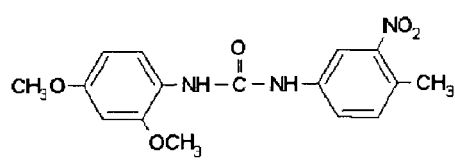 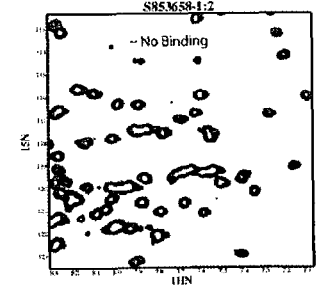
Figure 14

ANTIVIRAL INHIBITION OF CAPSID PROTEINS

CROSS REFERENCE TO RELATED APPLICATIONS

This application claims priority to U.S. provisional application No. 60/374,557 filed Apr. 22, 2002, U.S. provisional application No. 60/375,852 filed Apr. 25, 2002 and U.S. provisional application No. 60/404,043 filed Aug. 16, 2002.

GOVERNMENT LICENSE RIGHTS

The U.S. Government has a paid-up license in this invention and the right in limited circumstances to require the patent owner to license others on reasonable terms as provided for by the terms of grant no. AI30917 awarded by the National Institute of Health.

FIELD OF THE INVENTION

The invention relates to treatment of Acquired Immunodeficiency Syndrome (AIDS). In particular, the invention relates to treatment of AIDS by inhibition of the Human immunodeficiency virus type 1 (HIV-1) capsid protein.

BACKGROUND OF THE INVENTION

Viruses are noncellular infective agents that are capable of reproducing only in an appropriate host cell. Viruses are typically smaller than bacteria, and can infect animal, plant, or bacterial cells. Many viruses are important agents of disease. The infective particle (virion) consists of a core of nucleic acid surrounded by a proteinaceous capsid and, in some cases, an outer envelope.

Retroviruses are enveloped single-stranded RNA viruses infecting animals. The family consists of three groups: the spumaviruses such as the human foamy virus; the lentiviruses, such as the human immunodeficiency virus types 1 and 2, as well as visna virus of sheep; and the oncoviruses. The retrovirus particle is composed of two identical RNA molecules. Each genome is a positive sense, single-stranded RNA molecule, which is capped at the 5' end and polyadenylated at the 3' tail. The prototype C-type oncoviral RNA genome contains three open reading frames call gag, pol and env, bounded by regions that contain signals essential for expression of the viral genes. The gag region encodes the structural proteins of the viral capsid. The pol region encodes a viral proteinase as well as the proteins for genome processing, including reverse transcriptase, ribonuclease H and endonuclease enzymatic activities. The env region specifies the glycoproteins of the viral envelope. In addition to these three open reading frames, the more complex genomes of the lentiviruses and the spumaviruses carry additional open reading frames which encode regulatory proteins involved in the control of genome expression.

There are substantial homologies between the capsid proteins of both viruses and retroviruses. One of skill in the art can easily identify these homologies by searching any of the standard biotechnology search engines.

AIDS is a retroviral disease characterized by profound immunosuppression that leads to opportunistic infections, secondary neoplasms and neurologic manifestations. The magnitude of this modern plague is truly staggering. In the United States, AIDS is the leading cause of death in men between 25 and 44 years of age, and it is the third leading cause of death of women in this age group. Although initially recognized and reported in the United States, it has now been reported from more than 193 countries around the world. The pool of HIV-infected persons in Africa and Asia is large and rapidly expanding. Transmission of HIV occurs under conditions that facilitate exchange of blood or body fluids containing the virus or virus-infected cells. Hence, the three major routes of transmission are sexual contact, parenteral inoculation, and passage of the virus from infected mothers to their newborns. Because of the almost uniformly fatal outcome of AIDS, finding effective treatments for the disease remains a serious medical problem.

There is little doubt that AIDS is caused by HIV, a nontransforming human retrovirus belonging to the lentivirus family. O'Brien, et al., *HIV causes AIDS: Koch's postulates fulfilled*, Curr Opin Immunol 8:613 (1996). Two genetically different but related forms of HIV, called HIV-1 and HIV-2, have been isolated from patients with AIDS. HIV-1 is the most common type associated with AIDS in the United States, Europe, and Central Africa, whereas HIV-2 causes similar disease principally in West Africa.

Similar to most retroviruses, the HIV-1 virion is spherical and contains an electron-dense, cone shaped core surrounded by a lipid envelope derived from the host cell membrane. The virus core contains (1) the major capsid protein p24 (CA), (2) nucleocapsid protein p7/p9, (3) two copies of genomic RNA, and (4) the three viral enzymes (protease (PR), reverse transcriptase (RT), and integrase). The viral core is surrounded by a matrix protein called p17, which lies underneath the virion envelope. Studding the viral envelope are two viral glycoproteins, gp 120 and gp 41, which are critical for HIV infection of cells.

As with other retroviruses, the HIV proviral genome contains the gag, pol, and env genes, which code for various viral proteins. The products of the gag and pol genes are translated initially into large precursor proteins that must be cleaved by the viral protease to yield the mature proteins.

The CA is initially synthesized as a domain within a 55 kDa Gag precursor polyprotein. Approximately 4,000 copies of Gag assemble at the plasma membrane and bud to form an immature virus particle. Subsequent to budding, the CA is liberated by proteolytic cleavage of Gag, which triggers a conformational change that promotes assembly of the capsid particle. Gitti, et al., *Structure of the amino-terminal core domain of the HIV-1 capsid protein*, Science, 273: 231-35 (1996); von Schwedler, et al., *Proteolytic refolding of the HIV-1 capsid protein amino-terminus facilitates viral core assembly*, EMBO J., 17: 1555-68 (1998); Gross, et al., *N-terminal extension of human immunodeficiency virus capsid protein converts the in vitro assembly phenotype from tubular to spherical particles*, J. Virol., 72: 4798-4810 (1998). Two copies of the viral genome and enzymes essential for infectivity become encapsidated in the central, cone shaped capsid of the mature virion.

Several recent studies have shown that proper capsid assembly is critical for viral infectivity. Mutations in CA that inhibit assembly are lethal and mutations that alter capsid stability severely attenuate replication making the CA an attractive potential antiviral target. Tang, et al., *Human immunodeficiency virus type 1 N-terminal capsid mutants that exhibit aberrant core morphology are blocked in initiation of reverse transcription in infected cells*, J. Virol. 75: 9357-66 (2001); Reicin, et al., *The role of Gag in human immunodeficiency virus type 1 virion morphogenesis and early steps of the viral life cycle*, J. Virol., 70: 8645-52 (1996); and Forshey, et al., *Formation of a human immunodeficiency virus type 1 core of optimal stability is crucial for viral replication*, J. Virol. 76: 5667-5677 (2002).

Although antiviral agents have been developed that bind to the capsid protein of picornaviruses and suppress infectivity by inhibiting disassembly of the capsid shell, Smith, et al., *The site of attachment in human rhinovirus 14 for antiviral agents that inhibit uncoating*, Science, 233: 1286-93 (1986), inhibitors of HIV capsid assembly or disassembly have not yet been identified. Currently available drugs for the treatment of HIV infection target the RT and PR enzymes, two of fifteen proteins encoded by the viral genome. These drugs are marginally effective when administered independently due to the rapid emergence of resistant strains that are selected under conditions of incomplete viral suppression. Richman, D. D., *HIV chemotherapy*, Nature 410: 995-1001 (2001). Although sustained reductions in viral load can be achieved when inhibitors are used in appropriate combinations (highly affective anti-retroviral therapy, HAART), Richman, D. D., *HIV chemotherapy*, Nature 410: 995-1001 (2001); Pillay, et al, *Incidence and impact of resistance against approved antiretroviral drugs*, Rev Med Virol, 10: 231-53 (2000), inadequate suppression due to poor compliance, resistance, and interactions with other drugs or diet is a significant problem that limits the effectiveness of HAART therapy for many patients and can lead to the spread of drug-resistant strains. Mansky, et al, *Combination of drugs an drug-resistant reverse transcriptase results in a multiplicative increase of human immunodeficiency virus type 1 mutant frequencies*, J. Virol., 76: 9253-59 (2002); Coffin, J., *HIV population dynamic in vivo: implications for genetic variation, pathogenesis, and therapy*, Science, 267: 483-89 (1995); Kuritzkes, D. R., *Clinical significance of drug resistance in HIV-1 infection*, AIDS, 10: S27-33 (1996).

In spite of the availability of HAART therapy, the mortality and morbidities associated with AIDS remain significant and unresolved by current therapies. New therapeutic compounds and methods are needed that could reduce or ameliorate the adverse events and improve the clinical outcome of AIDS, including, for example, reducing mortality and improving the quality of life of those suffering from the disease.

SUMMARY OF THE INVENTION

The invention provides novel methods for evaluating the antiviral activity of test compounds. The method includes (a) contacting a test compound with $Gag^{283}$ or a fragment thereof, (b) determining the ability of the test compound to bind to the apical cleft near the C-terminal end of the N-terminal domain of the capsid protein, and (c) evaluating the antiviral effect of the test compound. The capsid protein can be a viral capsid protein or a retroviral capsid protein. The retroviral capsid protein includes, but is not limited to HIV-1 and HIV-2. The capsid protein can be immature or mature. In addition, the antiviral effect includes, but is not limited to, inhibition of capsid assembly during viral maturation and inhibition of disassembly during infectivity.

The invention also provides a method of reducing mortality associated with AIDS. The method includes administering a therapeutically effective amount of a compound that binds to the apical cleft near the C-terminal end of the N-terminal domain of the HIV capsid protein to a human suffering from AIDS. Compounds of the invention include, but are not limited to, N-(3-chloro-4-methylphenyl)-N'-[2-thioethyl-2'-[5-(dimethylaminomethyl)]-2-methylfuryl ]urea (CAP-1), N-(4-N-acetamidophenyl)-N'-(3-nitro-4-methyl phenyl) urea (CAP-2), N-(2-propyl)-N'-(3-nitro-4-methyl phenyl) urea (CAP-3), N-(3-chloro-4-methyl phenyl)-N'-(4-cyanophenyl) urea (CAP-4), N-(3-chloro-4-methyl phenyl)-N'-[4-(1,1,1-trichloromethyl)phenyl] urea (CAP-5), N-(3-nitro-4-fluorophenyl)-N'-[3-(1,1,1-trifluoromethyl) phenyl] urea (CAP-6), N-[(3-chloro-4-methyl phenyl)-N', N'-propyl] urea (CAP-7).

The invention also provides a method for treating a human suffering from AIDS. The method includes administering a compound that binds the apical cleft near the C-terminal end of the N-terminal domain of the HIV capsid protein in an amount effective to reduce the number and severity of morbidities associated with AIDS. Compounds of the invention include, but are not limited to, N-(3-chloro-4-methylphenyl)-N'-[2-thioethyl-2'-[5-(dimethylaminomethyl)]-2-methylfuryl ] urea (CAP-1), N-(4-N-acetamidophenyl)-N'-(3-nitro-4-methyl phenyl) urea (CAP-2), N-(2-propyl)-N'-(3-nitro-4-methyl phenyl) urea (CAP-3), N-(3-chloro-4-methyl phenyl)-N'-(4-cyanophenyl) urea (CAP-4), N-(3-chloro-4-methyl phenyl)-N'-[4-(1,1,1-trichloromethyl)phenyl] urea (CAP-5), N-(3-nitro-4-fluorophenyl)-N'-[3-(1,1,1-trifluoromethyl)phenyl] urea (CAP-6), N-[(3-chloro-4-methyl phenyl)-N',N'-propyl] urea (CAP-7).

The invention also provides a method of evaluating a test compound for the ability to inhibit β-hairpin formation of $Gag^{283}$. The method includes (a) contacting a test compound with $Gag^{283}$ or a fragment thereof, and (b) determining the ability of the compound to interfere with β-hairpin formation of $Gag^{283}$.

The invention also provides a method of screening a test compound for the ability to inhibit β-hairpin formation of $Gag^{283}$. The method includes (a) contacting the test compound with $Gag^{283}$ or a fragment thereof, and (b) determining the ability of the compound to interfere with β-hairpin formation of $Gag^{283}$.

The invention further provides a method of identifying a test compound for the ability to inhibit β-hairpin formation of $Gag^{283}$. The method includes (a) generating a 3D computer model of $Gag^{283}$ using $Gag^{283}$ molecular coordinates, and (b) using the model to identify a test compound that binds to $Gag^{283}$.

The invention further provides a method of identifying a test compound that binds to the apical cleft near the C-terminal end of the N-terminal domain of a capsid protein. The method includes (a) generating a 3D computer model of $Gag^{283}$ using $Gag^{283}$ molecular coordinates, and (b) using the model to identify a test compound that binds to the apical cleft. The capsid protein can be a viral capsid protein or a retroviral capsid protein. The retroviral capsid protein includes, but is not limited to HIV-1 and HIV-2.

The invention also provides for any derivative or pharmaceutically acceptable salts of CAP-1, CAP-2, CAP-2, CAP-3, CAP-4, CAP-5, CAP-6 or CAP-7 having the formula I described below that is an antiviral compound that binds to the apical site of the N-terminal domain of the HIV-1 capsid protein and inhibits proper assembly of the core particle. In particular, the invention provides derivatives or pharmaceutically acceptable salts of CAP-1 or its related molecules that contain a urea group that contain a substituted aromatic substituent on one nitrogen and a flexible tether attached to a second aromatic group on the other nitrogen.

BRIEF DESCRIPTION OF THE DRAWINGS

FIG. 7 is a tabular representation of structural statistics for the 20 lowest energy $Gag^{283}$ conformers.

FIG. 13 is a representation of an overlay of 2D $^1H$-$^{15}N$ HSQC spectra obtained for the HIV-1 capsid protein N-terminal domain upon titration with CAP-1, CAP-2, CAP-3 and CAP-4.

FIG. 14 is a representation of an overlay of 2D $^1H$-$^{15}N$ HSQC spectra obtained for the HIV-1 capsid protein N-terminal domain upon titration with CAP-5, CAP-6 and CAP-7.

DETAILED DESCRIPTION OF THE INVENTION

The CA of the mature HIV-1 contains an N-terminal β-hairpin that is essential for formation of the capsid core particle. CA is generated by proteolytic cleavage of the Gag precursor polyprotein during viral maturation. To date, high-resolution structural studies have focused on the proteins of the mature virus. The mature HIV-1 CA protein consists of N-terminal core ($CA^N$) and C-terminal dimerization ($CA^C$) domains that are folded independently and connected by a flexible linker. The $CA^N$ core domain contains a 13 residue N-terminal β-hairpin that is stabilized in part by a salt bridge between the terminal $NH_2^+$ group of Pro 1 and the side chain carboxyl group of Asp 51. These residues are highly conserved and it is likely that all other retroviruses except the spumaviruses contain a similar N-terminal β-hairpin. Mutagenesis studies indicate that the β-hairpin is required for the formation of HIV-1 capsid core particle and that it probably functions by participating directly in intermolecular CA-CA interactions.

The CA domain of Gag is also responsible for packaging about 200 copies of the host protein, CypA, which is a prolyl isomerase and a chaperone protein that is essential for HIV-1 infectivity. Although the precise function of CypA is not known, it is suspected that the protein facilitates disassembly of the capsid core during infectivity.

Figure 1:
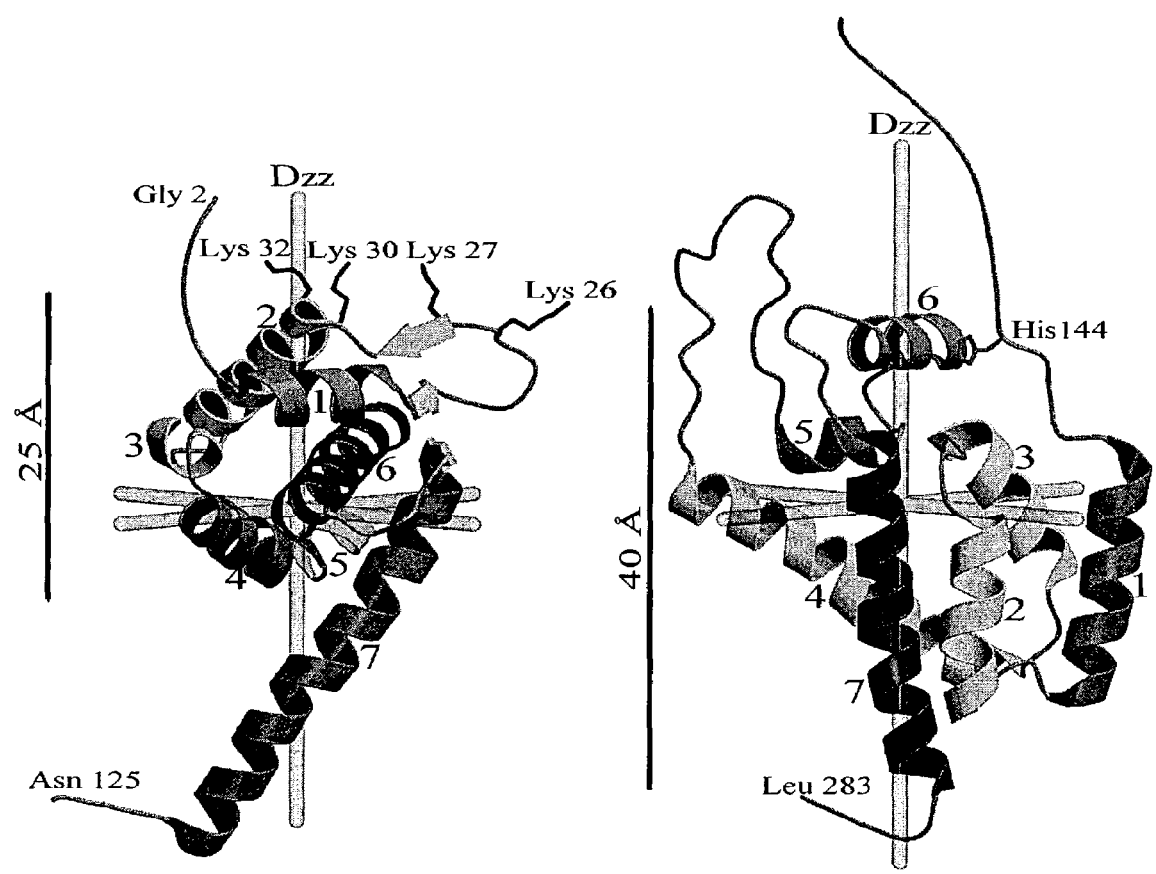
FIG. 1 is a representation of diffusion tensors determined independently for the MA and $CA^N$ domains of $Gag^{283}$. $D_{zz}$ denotes the principle component of the axially symmetric diffusion tensor.

Cryo-electron microscopic (EM) methods have been used to study the structure of the Gag polyprotein in immature virions and in virus-like particles. At low resolution, the assembled Gag proteins appear as an electron dense layer associated with the viral membrane. More recent studies have shown that the electron dense layer is actually composed of several spherical shells of density, including an outer shell associated directly with the lipid bilayer that corresponds to the MA domains of the Gag proteins, two shells corresponding to the $CA^N$ and $CA^C$ domains, and a fourth innermost shell that corresponds to the NC domain of Gag and the associated RNA genome. The thicknesses of MA and $CA^N$ shells correspond closely to the lengths (measured from N- to C-terminus) of the folded domains (FIG. 1). Interestingly, the separation between the MA and $CA^N$ shells is only 40 Å, even though the inventors' indicated that these domains can be separated by over 80 Å in extended forms of $Gag^{283}$. The separation could be even greater if the flexible C-terminal helix of MA is partially unfolded. This indicates that factors other than the length of the flexible linker define the separation of the shells in the immature particles and demonstrates that the MA and CA domains form ordered shells with defined protein-protein interactions.

Upon proteolytic maturation, the spherical CA shells of the immature virion condense to form the characteristic cone-shaped capsid core particle. The N-terminal β-hairpin is required for the formation of the capsid core particle. Mutations designed to inhibit β-hairpin formation in vivo, including Pro 133 to Leu and Asp 183 to Ala, result in the formation of virus particles that are unable to form normal capsid cores and are non-infectious. In addition, whereas native CA molecules can assemble into tubes that have some features resembling those of the native capsid core, addition of residues at the N-terminus of CA, or mutation of Asp 183 to Ala, lead to the formation of a heterogeneous mixture of structures that are generally spherical and resemble the capsid shells of immature virions. The β-hairpin makes extensive lattice contacts in crystal structures of both the intact CA protein bound to an antibody fragment, and to the CA$^N$ domain bound to CypA, suggesting that the β-hairpin promotes capsid assembly by participating directly in intermolecular CA-CA interactions.

The β-hairpin is unfolded in the immature protein and the β-hairpin formation occurs subsequent to proteolytic cleavage of Gag, triggering capsid assembly. Hairpin formation is stabilized by the salt bridge that can subsequently form between Pro 133-NH$_2^+$ and the COO— side chain of conserved Asp 183, as well as by numerous additional interactions that are not present in the immature protein. These additional interactions involve not only inter-β-strand hydrogen bonding and packing, but also interactions between the hairpin and the rest of CA$^N$ domain, including the new hydrogen bond between the backbone NH of Ile 134 and the carbonyl of Gly 178 and hydrophobic packing between the side chains of Ile 134 (β-hairpin), Thr 180 (helix 3) and Ile 247 and Met 250 (helix 6). Thus, the capsid assembly mechanism has features that appear very similar to those employed for enzyme activation by the trypsin family of serine proteases, in which proteolytic cleavage of the inactive zymogen results in a new N-terminal NH$_3^+$ group that forms a salt bridge with a buried carboxyl group and activates the enzyme.

The process of uncoating is dependent on the presence of CypA and CypA packaging by HIV-1 is essential for infectivity. Virions containing mutations in CA that abolish CypA binding are able to assemble and mature and appear normal in cryo-EM images. However, although these particles can fuse and penetrate target cells, they are unable to reverse-transcribe their genomes, indicating that CypA is necessary for an early event in the replication cycle that most likely occurs after virus maturation and membrane fusion. Interestingly, mutant virions that do not efficiently package CypA are infectious in cell lines that contain abnormally high intrinsic concentrations of CypA, and revertant mutants that arise spontaneously in the presence of cyclosporine analogs are dependent on these CypA inhibitors for infectivity. Taken together, these findings indicate that capsid assembly and disassembly processes are finely tuned and that relatively minor mutations or alterations in cellular conditions can affect the stability of the capsid core.

The NMR data described below indicates that β-hairpin formation induces an approximately 2 Å displacement of helix-6 and a concomitant shift of the CypA binding site. In view of the fact that (i) the β-hairpin is clearly important for capsid assembly, and (ii) CypA is likely involved in disassembly, conformational coupling between these sites is relevant to events associated with CypA-mediated uncoating. Thus, the binding of CypA to the exposed loop shifts the position of helix-6, resulting in either the destabilization or repositioning of the β-hairpin in a manner that destabilizes the capsid and promotes uncoating. NMR chemical shift mapping experiments revealed substantial shifts for the backbone amide signals of helix-6 upon CypA binding to the mature CA$^N$ domain. Although the β-hairpin of mature CA$^N$ is relatively mobile, its position is well defined in the NMR structure of the free domain.

Figure 2:
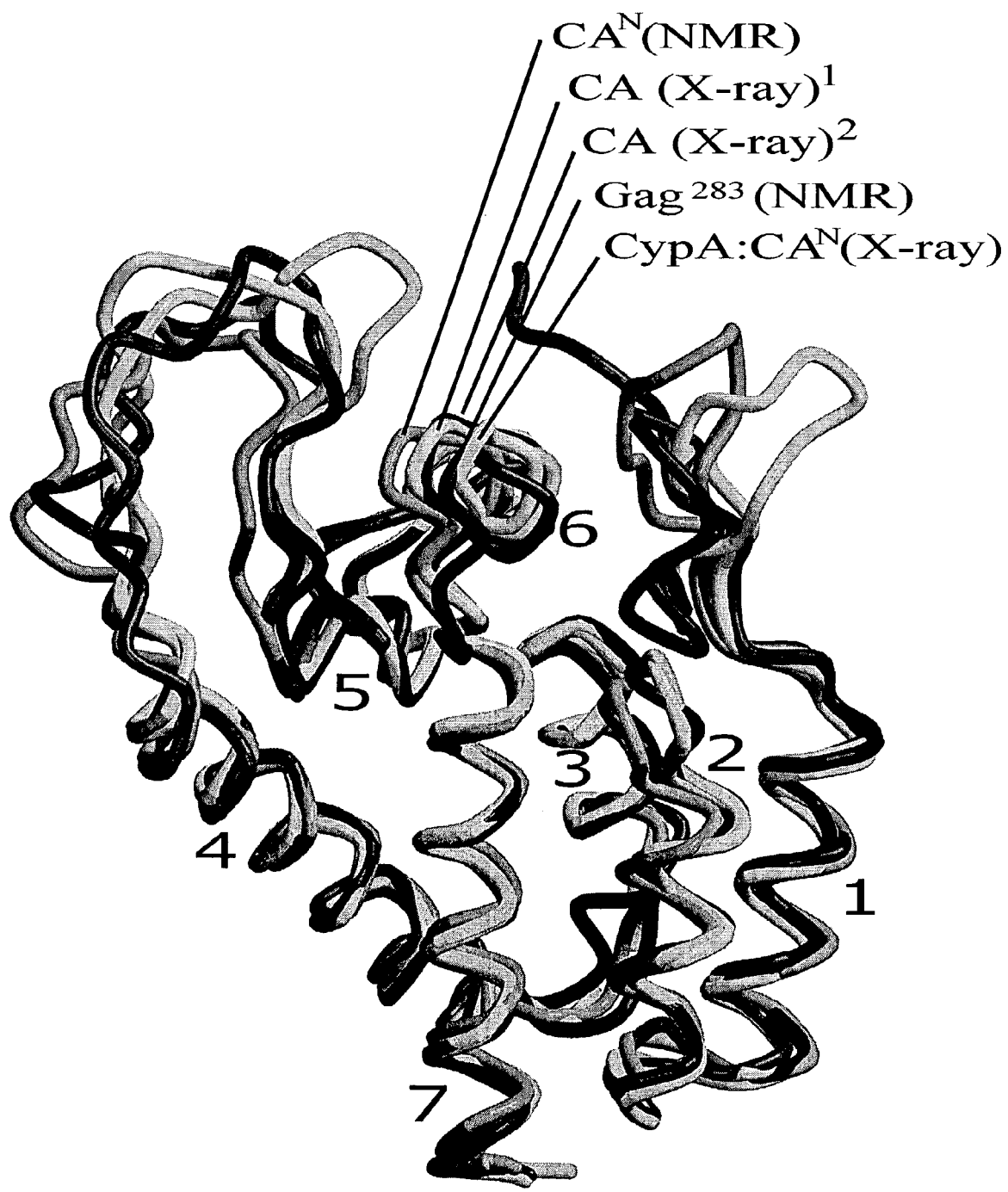
FIG. 2 is a comparison of the X-ray and NMR structures determined to date for the $CA^N$ domain of the HIV-1 capsid protein.

In contrast, in the X-ray crystal structure of the CypA-CA$^N$ dimer, well-defined electron density was observed for only one of the two β-hairpins. The missing electron density in the X-ray structure could therefore be at least partially due to the binding of CypA. Furthermore, comparison of the five X-ray and NMR structures that have been determined thus far for HIV-1 CA$^N$ domain revealed that the position of helix-6 can vary, depending on the conditions employed for structural studies (FIG. 2). Temperature factors reported for the backbone atoms of helix-6 are generally greater than those of the other helices in the high-resolution X-ray structure (2.36 Å) of the mature CA$^N$:CypA complex. Taken together, these data indicate that helix-6 is relatively mobile and that its position is sensitive to CypA binding and β-hairpin formation. Finally, the affinity of CypA for Gag is 1000-fold greater than its affinity for the mature capsid protein. These differences in affinity can be explained by the conformational coupling of the β-hairpin and CypA binding sites.

The three dimensional structure of the N-terminal half (residues 2-283) of the HIV-1 Gag polyprotein was determined using the following general methods. DNA encoding the N-terminal 283 residues of HIV-1 Gag precursor protein and an appended C-terminal His$_6$ tag was amplified from pNL4-3 plasmid using the polymerase chain reaction (PCR). Plasmid carrying Gag$^{283}$ was transformed into BL21 codon plus RIL cell line (Stratagene, La Jolla, Calif.). The transformed cells were grown on M9 minimum medium containing $^{15}$NH$_4$Cl and/or UL-[$^{13}$C]glucose (Cambridge Isotope Laboratories, Andover, Mass.) as its sole nitrogen and/or carbon source either in H$_2$O or in 99% $^2$H$_2$O (Martek, Columbia, Md.). Protein was purified with cobalt affinity resin (Clontech, Palo Alto, Calif.) in a single step. Typically, one liter of growth medium yields 20 mg Gag$^{283}$. Its molecular weight was confirmed by ESI-MS.

NMR data were collected with 1 mM protein samples containing 50 mM sodium acetate buffer at pH 5.0, 100 mM NaCl, 5 mM βMercaptoethanol and 1× protease inhibitor cocktail (Calbiochem, San Diego, Calif.). All NMR studies were carried out with a 600 MHZ Bruker AVANCE DRX spectrometer equipped with xyz-gradients triple resonance probe; T=30° C., 2D $^{15}$N HSQC, 3D constant time HNHA, HN(CO)CA, HNCO, and 4D $^{15}$N/$^{15}$N-edited NOESY (4DNN) data were used for backbone assignments. The 4DNN data were obtained for a U-$^2$H/$^{15}$N labeled sample; T$_{mix}$=200 ms. Other NOE data collected on U-$^{13}$C/$^{15}$N labeled sample include 4D $^{13}$C/$^{15}$N-edited NOESY (T$_{mix}$=120 ms) and 4D $^{13}$C/$^{13}$C-edited NOESY (T$_{mix}$=100 ms recorded in $^2$H$_2$O). NMR data was processed with NMRPipe and analyzed in NMRView. Signals were assigned using standard assignment strategies.

The NOE cross-peaks were quantitatively categorized as strong, medium and weak and used to assign upper distance limits of 2.7, 3.2 and 5.0 Å, respectively. Distance involving methyl groups, degenerate germinal methylene groups, degenerate aromatic protons and non-stereo-specifically assigned methyl groups of leucine or valine were compensated by adding 0.5, 0.8, 2.3 and 1.5 Å, respectively. Backbone hydrogen bond restraints (1.8-2.7 Å for H—O distances and 2.4-3.2 Å for N—O distances) were implemented to reinforce canonical secondary structures based on characteristic NOE patterns and chemical shift indices.

Backbone dihedral angle restraints were obtained by analysis of $^{13}$C$^\alpha$, $^{13}$C$^\beta$, $^1$H$^\alpha$, $^{13}$C and $^{15}$N chemical shifts using the program TALOS. Structure calculations performed with DYANA were initially carried out using only distance restraints derived from the NOE data. Hydrogen bond and dihedral angle restraints were subsequently incorporated and target functions were further minimized. The quality of the generated structures was assessed with Procheck-NMR. Images were generated with Chimera and MolScript and rendered with Raster 3D.

$^{15}$N relaxation data were for U-$^2$H/$^{15}$N labeled Gag$^{283}$ samples prepared under conditions described above. {$^1$H}-$^{15}$N steady state heteronuclear NOE (XNOE) for backbone $^{15}$N nuclei were measured with inverse detected water flip-back pulse sequence. Longitudinal relaxation rates R$_1$ and transverse relaxation rates $R_2$ were measured by collecting eight two-dimensional spectra at different delays in an interleaved mode. The eight delays for $^{15}N$ $T_1$ ($=1/R_1$) are 10.04, 120.49, 512.09, 763.12, 1004.11, 1506.16, 2008.21, 2510.26 ms and for $^{15}N$ $T_2$($=1/R_2$) are 21.10, 36.70, 52.30, 67.89, 83.49, 99.09, 114.69, 130.29 ms; 4 s recovery delay.

The XNOE value of a given residue was derived from the intensity ratio ($I/I_0$) of $^{15}N/^1H$ correlation peak in the presence of proton saturation (I) and in the absence of proton saturation ($I_0$). Errors were estimated from the baseline noise. Relaxation rates for each well-resolved peak were obtained by fitting peak intensities of eight spectra into two parameter ($R_2$) or three-parameter exponential ($R_1$) decay using commercial software Orgin 6.0 (microcal, Northampton, Mass.). Reported errors are calculated during the filling of the relaxation data. NH groups exhibiting significant internal motions at ps-ns timescale (XNOE<0.70) or chemical exchange on μs-ms timescale (significant increase of $R_2$ without concomitant increase in $R_1$) were excluded from rotational diffusion calculations, and the remaining relaxation data were analyzed with Quadric Diffusion 1.12 (A. G. Palmer, Columbia University).

NMR chemical shift assignments for Gag$^{283}$ have been deposited with the BioMagResBank accession number 5316. Coordinates for the 20 conformers with lowest target functions, and the associated restraint list, have been deposited in the Protein Data Bank accession number 1L6N. The restraint list and coordinates for the refined structure of the mature $CA^N$ domain have also been deposited, accession number (1GWP).

The three dimensional structure of the N-terminal half (residues 2-283) of the HIV-1 Gag polyprotein revealed a surface cleft that is exposed on the CA domain of the immature protein but becomes filled by residues of an N-terminal β-hairpin of the CA protein upon proteolytic maturation. Compounds that bind to the β-hairpin cleft inhibit viral maturation and possess antiviral activity.

Further studies revealed an addition binding site (apical cleft) near the C-terminal end of the N-terminal domain of CA. Unlike the β-hairpin pocket, the apical cleft is present on both the mature and immature forms of the N-terminal domain of CA. Compounds that bind to this apical cleft inhibit capsid assembly and have antiviral properties. Residues of CA with backbone amide signals that are most significantly perturbed by binding of inhibitors to the apical cleft are either strictly conserved (Glu 35, Val 36, Val 59, Gly 60, His 62, Gln 63, Ala 65, Tyr 145) or rarely and conservatively substituted (number of occurrences in parentheses: E29D (2) K30R (1), A31G (16,), A31N (1), F32L (1), SeeN (13), G61E (1), M144T (1)) among the 93 genome sequences in the HIV Sequence Compendium. Most of the conserved residues are exposed on the surface of the N-terminal domain suggesting a possible macromolecular interactive function. Residues of the apical cleft of the N-terminal domain participate in an intermolecular CA (N-terminal domain)—CA (C-terminal domain) interface upon in vitro capsid formation. This, in combination with the other disclosures contained herein, provides compelling evidence that the inhibitor compounds function mechanistically by inhibiting intermolecular CA-CA interactions necessary for proper capsid assembly.

Residues Trp 23 and Val 59 exhibit significant chemical shift changes upon inhibitor ligand binding despite the fact that they are buried between helices 1, 2 and 3 of the CA monomer. It is, therefore, likely that the assembly inhibitors alter the local structure of the capsid protein and may thereby either competitively inhibit CA-CA interactions or promote the formation of a structurally distorted capsid shell.

Inhibition of capsid assembly does not require ligands with exceptionally high affinity for CA. This is likely due to the high local concentration of Gag molecules in assembled virions (14 mM), which favors binding by ligands with even modest affinities, e.g., N-(3-chloro-4-methylphenyl)-N'-[2-thioethyl-2'-[5-(dimethylaminomethyl)]-2-methylfuryl]urea (CAP-1). Thus conservatively assuming that cytosolic drug concentrations in the budding virus and cells are equal (100 μM), the percentage of viral CAP-1 molecules bound to CA can be estimated by standard mass action calculations which affords a value for the concentration of bound CAP-1 ([CA:CAP-1]) of 94 μM. This indicates that 94% of the CAP-1 molecules in immature virions (100 μM dose) should be bound to Gag, and that binding to as few as approximately 25 molecules of Gag per virion is sufficient to inhibit core assembly during viral maturation.

Figure 3:
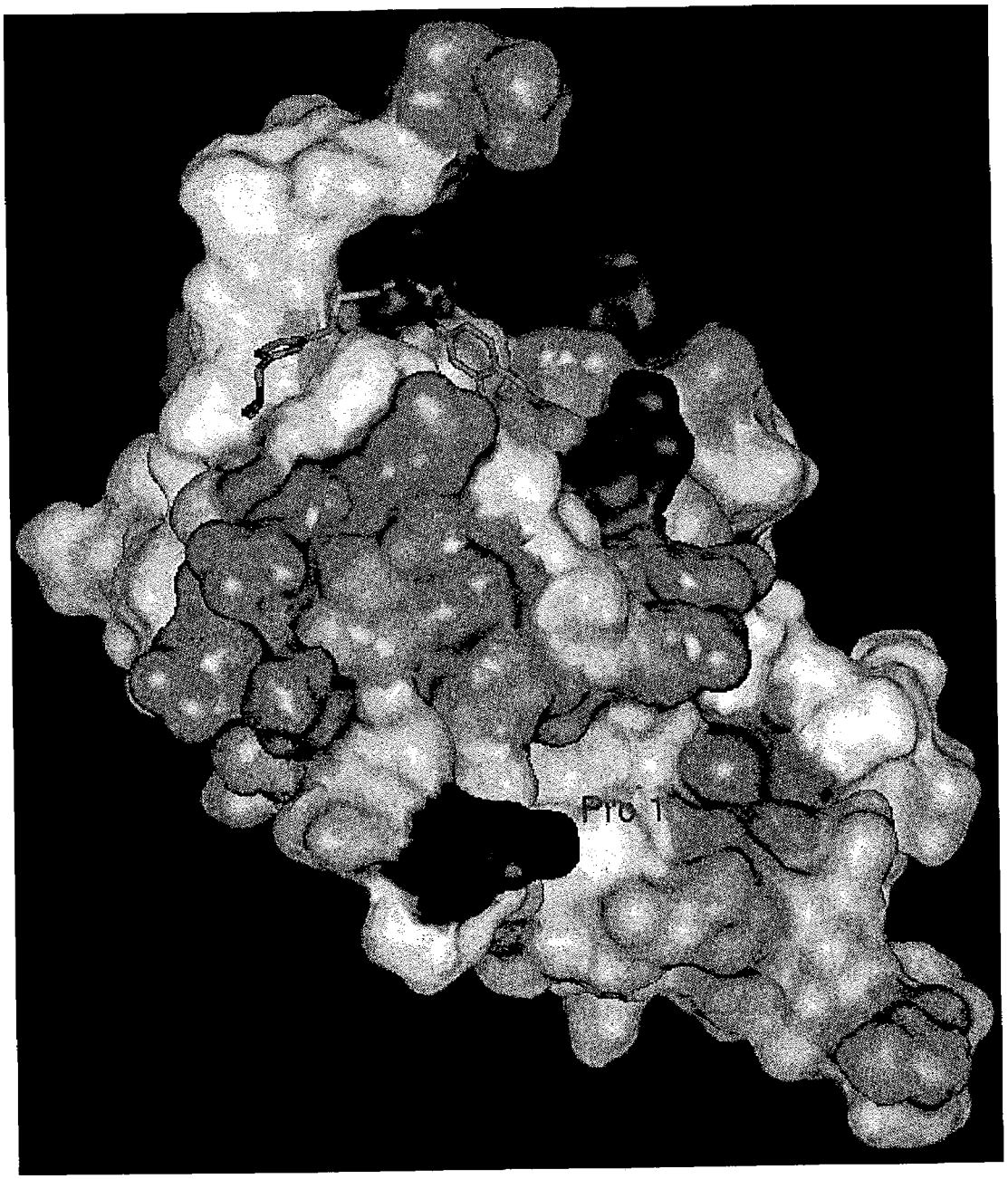
FIG. 3 is a representation of CAP-1 docked in the apical cleft of the HIV-1 capsid protein.

FIG. 3 shows the small molecule ligand CAP-1 docked in the structure of the capsid protein. The experimentally determined NMR structure of the capsid protein is utilized to generate the Connoly surface. The wireframe model of the ligand is illustrated in green. The ligand structure is minimized with appropriate ab initio methods. The capsid structure is colored to represent hydrophobicity (blue, most hydrophobic; red, most hydrophilic; white, intermediate hydrophobicity).

Figure 4:
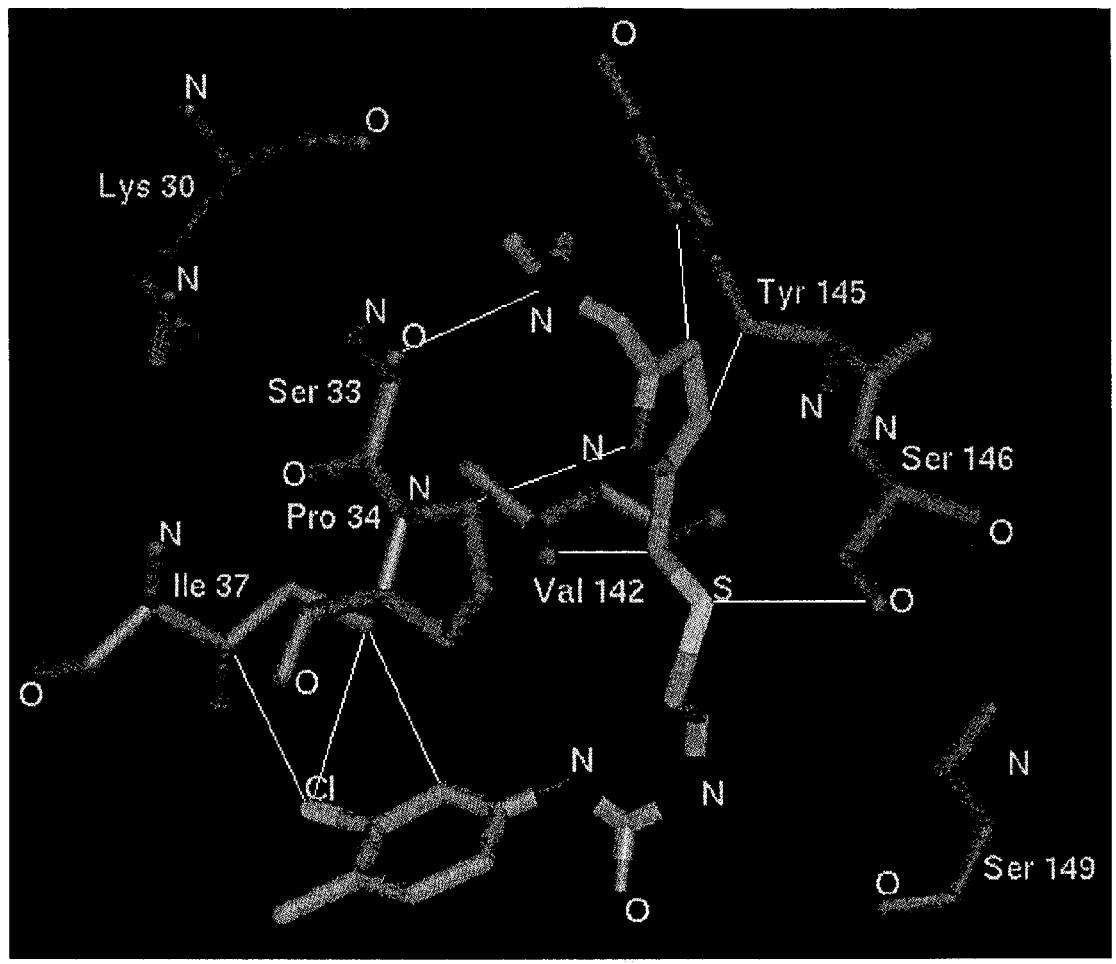
FIG. 4 is a representation of the short-range interactions involved in the binding of CAP-1 to the apical cleft of the HIV-1 capsid protein.

The experimentally determined important interactions are shown in FIG. 4. Notable is the interaction between the aromatic ring of Tyr 145 and the furan of CAP-1; the chlorine of the aromatic ring in CAP 1 and the hydrophobic sidechain of Ile 37; the interaction of the sulfur in the disulfide component of the molecule and the hydroxyl group of Ser 146; and the hydroxyl sidechain of Ser 33 and the nitrogen of the dimethylaminomethyl substituent on the 5-position of the furan of CAP 1.

Other ureas including all of those described in the present application are experimentally determined to possess functionally very similar interactions with the capsid protein. This is evident from the two-dimensional NMR data presented in FIGS. 13-14, below.

The data from the examination of the multidimensional NMR spectra of the capsid protein in the presence of the ligands CAP-1 and its structural homologues demonstrate the existence of a potentially high affinity binding site for ligands. A multiplicity of specific and selective interactions were unexpectedly found which not only demonstrate the existence of such a site, but help to suggest how very high affinity ligands might be designed for the site.

It is observed that several structural features represent requirements for the ligand. It is necessary to have a substituted phenyl or other aryl group on one side of the molecule, which contains a relatively bulky substituent. In the present situation, the chlorine atom serves this purpose. However, the experimental data combined with model fitting suggest that the use of a Br- or even I-atom might increase the affinity of binding. Other substituents on this aromatic ring are not as clearly indicated in terms of position, but the binding site model would be positively effected, in our view, with the inclusion of a substituent such as cyano or dialkylamino ortho-to the halogen. The 3,4-dichlorophenyl or 3-chloro-4-bromo phenyl moieties also would be active.

The relative position of the sulfur atom in CAP-1 is highly significant. It is probable that using a different oxidation state of the sulfur would not lend itself to activity in the present system. This is true for a sulfone or sulfonamide.

The furan could equally be replaced with a variety of heterocyclic groups with various substituents on the sidechain. In addition to the dimethylaminomethyl, replacement of this group with groups such as guanidine, N-cyanoguanidine, N-nitroguanidine, and such would probably yield active compounds.

Compounds with higher affinity for cytosolic Gag will be concentrated in assembling viruses, and compounds with greater affinity for CA are more potent inhibitors of in vitro assembly. It is therefore possible to rationally design agents with increased potency as antiviral inhibitors of HIV-1 capsid assembly.

Derivatives of CAP-1, CAP-2, CAP-2, CAP-3, CAP-4, CAP-5, CAP-6 or CAP-7 that are antiviral compounds that bind to the apical site of the N-terminal domain of the HIV-1 capsid protein and inhibit proper assembly of the core particle are also disclosed. In particular, the invention provides derivatives of CAP-1 or its related molecules that contain a urea group that contains a substituted aromatic substituent on one nitrogen and a flexible tether attached to a second aromatic group on the other nitrogen. For example, such derivatives are compounds or pharmaceutically acceptable salts having formula I:

[I]

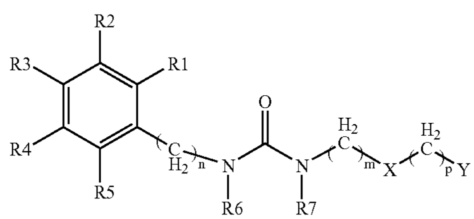

wherein:

(a) $R_1$ represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NHCHR_8COOH$, —$NHCR_8R_9COOH$, —$NR_8COOR_9$, —$COOR_8$ or a hydrocarbon group comprising a straight chained, branched or cyclic group each containing up to 9 carbon atoms;

(b) $R_2$ represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NHCHR_8COOH$, —$NHCR_8R_9COOH$, —$NR_8COOR_9$, —$COOR_8$ or a hydrocarbon group comprising a straight chained, branched or cyclic group each containing up to 9 carbon atoms;

(c) $R_3$ represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NHCHR_8COOH$, —$NHCR_8R_9COOH$, —$NR_8COOR_9$, —$COOR_8$ or a hydrocarbon group comprising a straight chained, branched or cyclic group each containing up to 9 carbon atoms;

(d) $R_4$ represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NHCHR_8COOH$, —$NHCR_8R_9COOH$, —$NR_8COOR_9$, —$COOR_8$ or a hydrocarbon group comprising a straight chained, branched or cyclic group each containing up to 9 carbon atoms;

(e) $R_5$ represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NHCHR_8COOH$, —$NHCR_8R_9COOH$, —$NR_8COOR_9$, —$COOR_8$ or a hydrocarbon group comprising a straight chained, branched or cyclic group each containing up to 9 carbon atoms;

(f) Halogen is limited to fluoro, chloro, bromo, and iodo (g) $R_8$ and $R_9$ are independently methyl, ethyl, n-propyl, i-propyl, n-butyl, i-butyl, sec-butyl, t-butyl, pentyl, hexyl, neo-pentyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclohexylmethyl, or cyclohexylethyl (h) The letters n, m, and p represent independently any integer from 1 to 6

(i) $R_6$ and $R_7$ are independently selected from the group consisting of hydrogen or a hydrocarbon group comprising a straight chained, branched or cyclic group each containing up to 6 carbon atoms (j) X is selected from the group consisting of O or S (k) Y is heterocyclic, carbocyclic, or optionally substituted phenyl.

(l) Heterocyclic is selected from any stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl, and fused ring and spiro compounds containing the above heterocycles.

(m) carbocyclic is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0] bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

(n) Substituted phenyl is defined by formula II $$\text{II}$$

[structure of benzene ring with substituents R10, R11, R12, R13, R14]

wherein:

(o) $R_{10}$ represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NR_8COOR_9$, —$COOR_8$ or a hydrocarbon group comprising a straight chained, branched or cyclic group each containing up to 9 carbon atoms;

(p) $R_{11}$ independently represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NR_8COOR_9$, —$COOR_8$ or a hydrocarbon group comprising a straight chained, branched or cyclic group each containing up to 9 carbon atoms;

(q) $R_{12}$ independently represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NR_8COOR_9$, —$COOR_8$ or a hydrocarbon group comprising a straight chained, branched or cyclic group each containing up to 9 carbon atoms;

(r) $R_{13}$ independently represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NR_8COOR_9$, —$COOR_8$ or a hydrocarbon group comprising a straight chained, branched or cyclic group each containing up to 9 carbon atoms;

(s) $R_{14}$ independently represents hydrogen, halogen, cyano, trifluoromethyl, trichloromethyl, nitro, —$OR_8$, —$SR_8$, —$NHR_8$, —$NR_8R_9$, —NHCOOH, —$NHCH_2COOH$, —$NR_8COOR_9$, —$COOR_8$ or a hydrocarbon group comprising a straight chained, branched or cyclic group each containing up to 9 carbon atoms;

(t) $R_8$ and $R_9$ are independently methyl, ethyl, n-propyl, i-propyl, n-butyl, i-butyl, sec-butyl, t-butyl, pentyl, hexyl, neo-pentyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclohexylmethyl, or cyclohexylethyl (u) Halogen is limited to fluoro, chloro, bromo, and iodo.

Therapeutic compositions comprising compounds that bind to the apical cleft of HIV-1 capsid protein may be administered systemically or topically. Systemic routes of administration include oral, intravenous, intramuscular or subcutaneous injection (including into a depot for long-term release), intraocular and retrobulbar, intrathecal, intraperitoneal (e.g., by intraperitoneal lavage), intrapulmonary using aerosolized or nebulized drug, or transdermal. Topical routes include administration in the form of salves, ophthalmic drops, eardrops, irrigation fluids (for, e.g., irrigation of wounds) or medicated shampoos. Those skilled in the art can readily optimize effective dosages and administration regimens for therapeutic compositions comprising compounds that bind to the apical cleft of HIV-1 capsid protein, as determined by good medical practice and the clinical condition of the individual patient.

The administration of compounds that bind to the apical cleft of HIV-1 capsid protein is preferably accomplished with a pharmaceutical composition comprising such a compound and a pharmaceutically acceptable diluent, adjuvant or carrier. The compound may be administered without or in conjunction with known surfactants, other chemotherapeutic agents or additional known antiviral agents.

Other aspects and advantages of the invention will be understood upon consideration of the following illustrative examples. Example 1 describes the overall structure and dynamics of $Gag^{283}$. Example 2 describes the structure of the MA domain of $Gag^{283}$. Example 3 describes the structure of the $CA^N$ domain of $Gag^{283}$. Example 4 describes the identification of the ligand binding site on the N-terminal domain of CA. Example 5 describes the in vitro inhibition of capsid assembly by compounds that bind to the apical cleft of HIV-1 capsid protein. Example 6 describes the inhibition of viral infectivity by compounds that bind to the apical cleft of HIV-1 capsid protein. Example 7 describes the in vivo inhibition of capsid assembly.

EXAMPLE 1

The Overall Structure and Dynamics of $Gag^{283}$

A 32.2 kD recombinant polypeptide ($Gag^{283}$) corresponding to the 283 N-terminal residues of HIV-$1_{pNL4-3}$ (plus an additional C-terminal hexahistidine tag) was cloned and prepared for NMR studies ($Mr_{calc}$=32216.6 Daltons, $Mr_{exp}$=32216.1±0.8 Daltons. High quality NMR spectra were obtained (FIG. 5), enabling nearly complete $^1H$, $^{15}N$ and $^{13}C$ NMR signals assignments. NMR chemical shifts of the backbone atoms are indicative of a highly helical structure (FIG. 6).

Residues Gly 2-Ser 6, Gly 123-Val 143 and Pro 279-Leu 283 exhibit relatively low {$^1H$}-$^{15}N$ heteronuclear NOE (XNOE) and $T_2$ relaxation values (FIG. 6), as well as few or no medium range $^1H$-$^1H$ NOEs, indicating that these residues are conformationally labile. A total of 2,376 experimentally derived restraints (2046 distance restraints and 332 torsion angle restraints, corresponding to 17.7 restraints per restrained residue) were employed for the relatively non-labile residues Val 7-Thr 122 and His 144-Ser 278. Twenty refined structures with target functions of 1.50±0.24 Å$^2$ and good structural statistics (FIG. 7) were generated with DYANA. Residues VAL 7-Thr 122 of MA and His 144-Ser 278 of CA$^N$ exhibit good convergence, with pairwise RMS deviations for backbone heavy atoms of the helices of 0.41±0.09 and 0.72±0.14 Å, respectively. Since no restraints were employed for the mobile residues that connect the folded domains (Gly 123-Val 143), and no NOEs were observed between the domains, the relative orientation of the MA and CA$^N$ domains is not defined. The calculations indicate that the two domains can be separated by up to 80 Å when residues Gly 123-Val 143 are fully extended.

Figure 8:
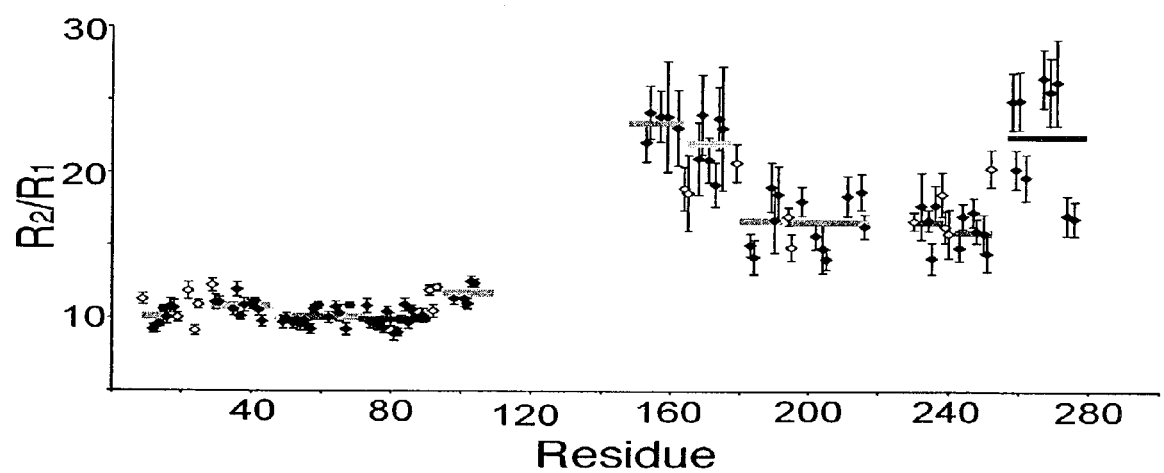
FIG. 8 is a representation of backbone $^{15}N$ $R_2/R_1$ values determined for residues that exhibit neither significant internal mobility nor conformational exchange.

The $T_1/T_2$ ratios obtained for the backbone NH groups indicate that the MA and CA$^N$ domains tumble with different rotational correlation times. For both domains $T_1/T_2$ (=$R_2$/$R_2$) ratios for residues of the different helices were generally clustered, which is indicative of anisotropic rotational diffusion, (FIG. 8). Errors associated with the $T_1/T_2$ ratios of the CA$^N$ domain are somewhat larger than those of the MA domain due to the larger line widths of the CA$^N$ signals (and corresponding smaller signal-to-noise ratio) (FIG. 6). The relatively poor clustering observed for some helices of the CA$^N$ domain (especially helix 7) is likely due to the presence of weak CA$^N$-CA$^N$ intermolecular interactions. Indeed the scatter in $T_1/T_2$ ratios for a given helix decreased as sample concentrations were reduced from 1.0 to 0.25 mM, but the average $T_1/T_2$ ratios were essentially unaffected. The rotational diffusion properties of the MA and CA$^N$ domains were calculated independently. Best statistical fits were obtained using prolate axially symmetric diffusion models, which afforded rotational correlation times of 10.0±0.1 ns and 13.2±0.2 ns for the MA and CA$^N$ domains, respectively. The principal axes of the diffusion tensors (i.e., the axes about which rotational diffusion is fastest) are nearly coincident with vectors that connect the N- and C-terminal residues of the folded domains (FIG. 1).

EXAMPLE 2

Structure of the MA Domain of Gag$^{283}$

The structure of the MA domain of Gag$^{283}$ was essentially identical to that observed for the isolated, mature protein. Superposition of the backbone heavy atoms of rigid residues of the mature and immature MA NMR structures afforded pairwise RMS deviations of 1.27±0.005 Å. The structure was in better agreement with the X-ray structure of the mature MA trimer (1.14±0.09 Å) due to the use of more modern methodologies in the current NMR study (i.e., chemical shift-based restraints and the use of 4D NMR data). The fit improved to 0.90±0.11 Å when a $3_{10}$ helix that undergoes conformational changes upon trimerization (Pro 66-Gly 71) was removed from the fitting with the X-ray structure. The $^1H$-$^1H$ NOE data indicated that the C-terminal helix extends beyond the globular portion of the domain to residue Thr 122. However, the $C_\alpha$ chemical shift indices progressively decreased from helical to random coil values for residue Ile 104-Gln 117, and together with the relaxation data indicated a progressive shift from predominantly α-helical to predominantly random coil conformations (FIG. 4). This finding was consistent with X-ray structural data reported for the mature MA trimer, in which electron density for these residues varied substantially among the six different molecules of the unit cell.

EXAMPLE 3

Structure of the CA$^N$ Domain of Gag$^{283}$

The overall structure of the CA$^N$ domain of Gag$^{283}$ is very similar to that observed for the mature CA$^N$ domain. To facilitate comparisons, the amino acid numbering scheme of immature CA$^N$ was also used for the mature domain (i.e., Pro 133 is the N-terminal residue of mature CA$^N$). Residues Ser 148-Lys 162, Ser 165-Ser 176, Thr 180-Val 191, His 194-His216, Arg 232-Ala 237, Thr 242-Thr 251, Val 258-Ser 278 form seven α-helices (helix 1-7, respectively) that are packed together in a flat and triangular shape, and residues Pro 217-Pro 231 (which include the CypA binding site) form a conformationally flexible loop. Superposition of the backbone heavy atoms of the helical residues of the mature and immature forms of CA$^N$ NMR structures afford pairwise RMS deviations of 1.32±0.13 Å.

In contrast, the conformation of residues Pro 133-Val 143 of Gag$^{283}$ is substantially different from that observed in the mature CA$^N$ protein. No intermediate of long-range $^1H$-$^1H$ NOEs were observed for these residues, and the chemical shift index data indicated that they exist in a random coil conformation (FIG. 6). Also, the $^{15}N$ NMR relaxation properties of these residues indicated a high degree of conformational mobility (FIG. 6). In the mature CA$^N$ domain, residues Pro 133-Asn 137 pair with residues Gln 141-Gln 145 to form anti-parallel strands of a β-hairpin that packs against helix-6, and the backbone $NH_2^+$ group of Pro 133 forms a salt bridge with the partially buried side chain of Asp 183. In addition, although residues His 144-Ile 147 interact with globular portion of the CA$^N$ domain in both the immature and mature structures, differences in the NOE data indicated subtle but significant structural differences. For example, in the mature CA$^N$ domain, the His 144-Hβ protons exhibited moderate intensity NOEs with the side chain methyl protons of Ile 247 (helix 6), whereas these groups give rise to very weak NOEs in the mature domain.

Figure 9:
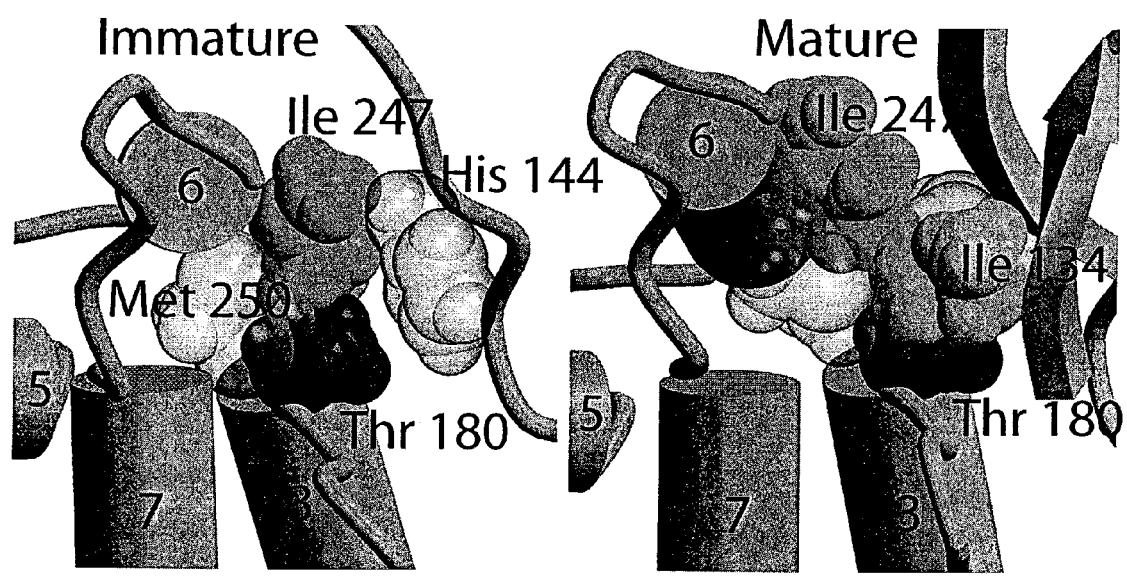
FIG. 9 is a comparison of the NMR structures determined for $CA^N$ and $Gag^{283}$ showing conformational differences associated with helix 6.
Figure 10:
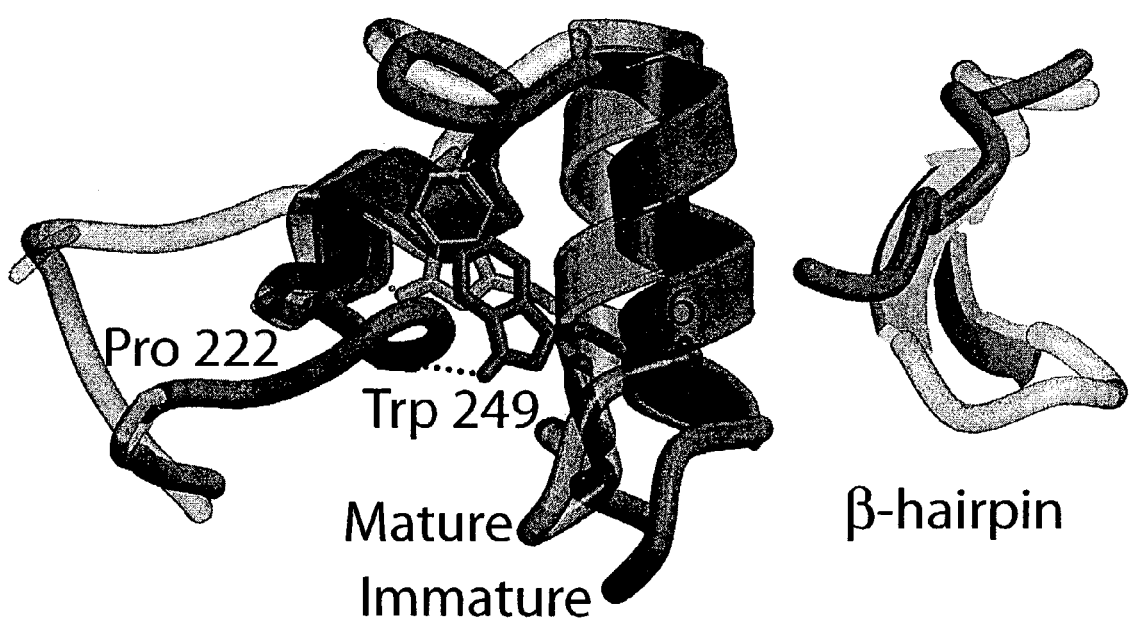
FIG. 10 is a representation of the shift of helix 6 and the concomitant change in the position of the CypA binding loop.
Figure 11:
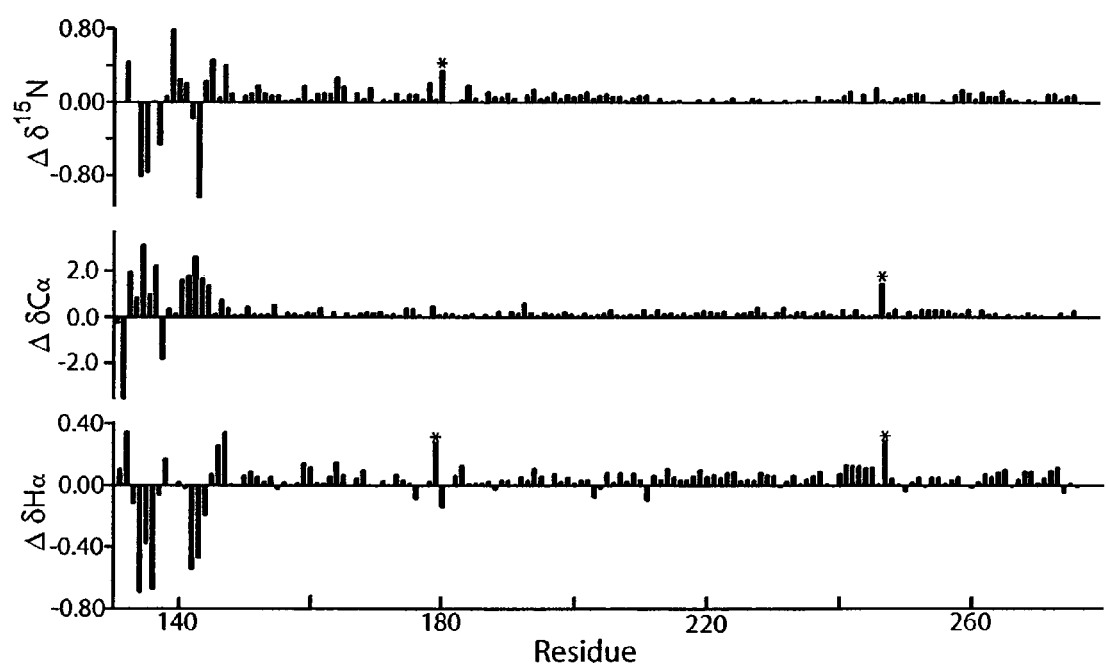
FIG. 11 is a representation of the chemical shift differences observed for the backbone atoms of the immature and mature $CA^N$ domains.

In addition, helix 6 was shifted by approximately 2 Å relative to its position in the mature protein (FIGS. 10 and 11). In the immature domain, the side chain of Thr 180, which caps helix 3, packs within a hydrophobic cluster formed by the side chains of Leu 243, Ile 247 and Met 250 of helix 6 (FIG. 9), and very strong $^1H$-$^1H$ NOEs were observed between the Thr 180 and Ile 247 methyl groups. However, in the mature protein, the side chain of Ile 134 is inserted into this hydrophobic pocket, resulting in an approximately 2 Å separation of the Thr 180 and Ile 247 side chains and a substantial reduction in the intensities of the associated inter-residue NOEs.

Furthermore, the $\chi_2$-angle of the Leu 243 side chain differs by an approximately 90° rotation, and the methyl group of Met 250 is reoriented in the immature domain in a manner to partially fill the space occupied by the Ile 134 side chain of the mature domain (FIG. 9). Helix 6 also makes contact with the CypA binding loop. Although the loop is flexible, a qualitative comparison of the two ensembles of NMR structures indicated that Pro 222, which binds to the active site of CypA, was shifted by several angstroms relative to its position in the mature $CA^N$ domain (FIG. 10). Significant $^1H$, $^{15}N$ and $^{13}C$ chemical shift differences were observed for residues Pro 133-Ile 147, which were extended in the immature protein but form a β-hairpin in the mature domain (FIG. 11). Significant shifts were also observed for Ala 179, Thr 180, Ile 243, Ile 247, Met 250 and Leu 243, which interact with the β-sheet in the mature $CA^N$ domain. These shift differences are fully consistent with the structural changes described above.

Figure 5:
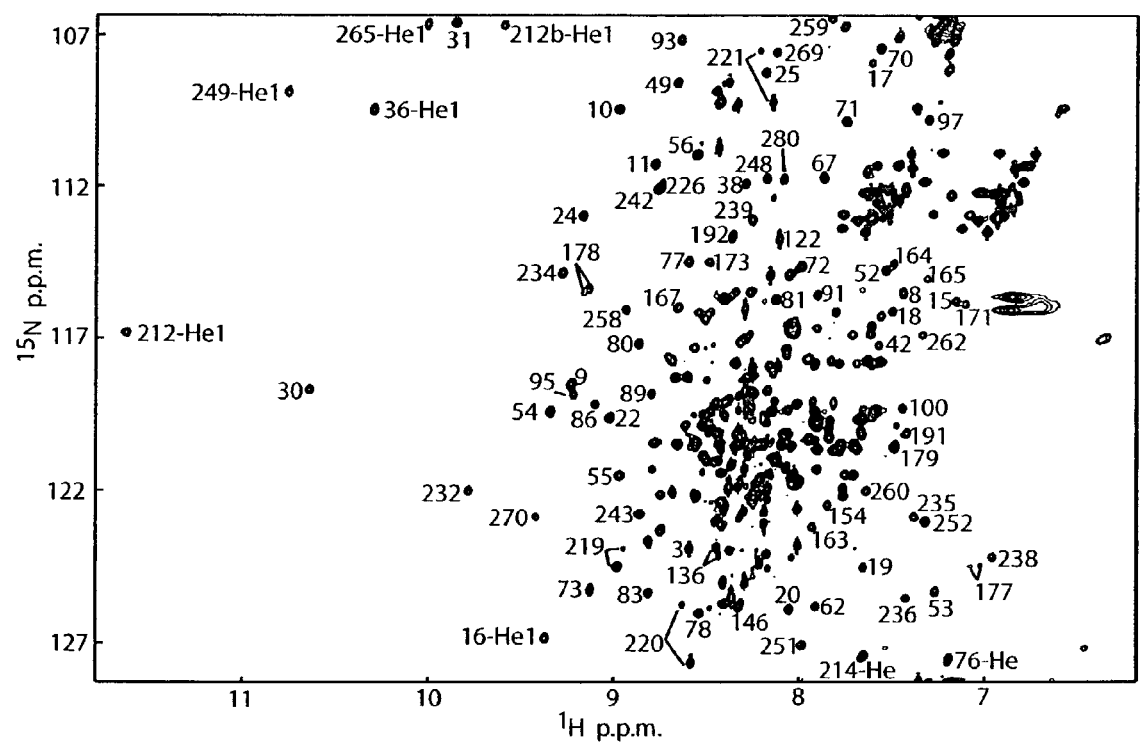
FIG. 5 represents a resolution enhanced $^1H$-$^{15}N$ HSQC spectrum obtained for a $^2H$, $^{15}N$-labeled $Gag^{283}$ sample.
Figure 6:
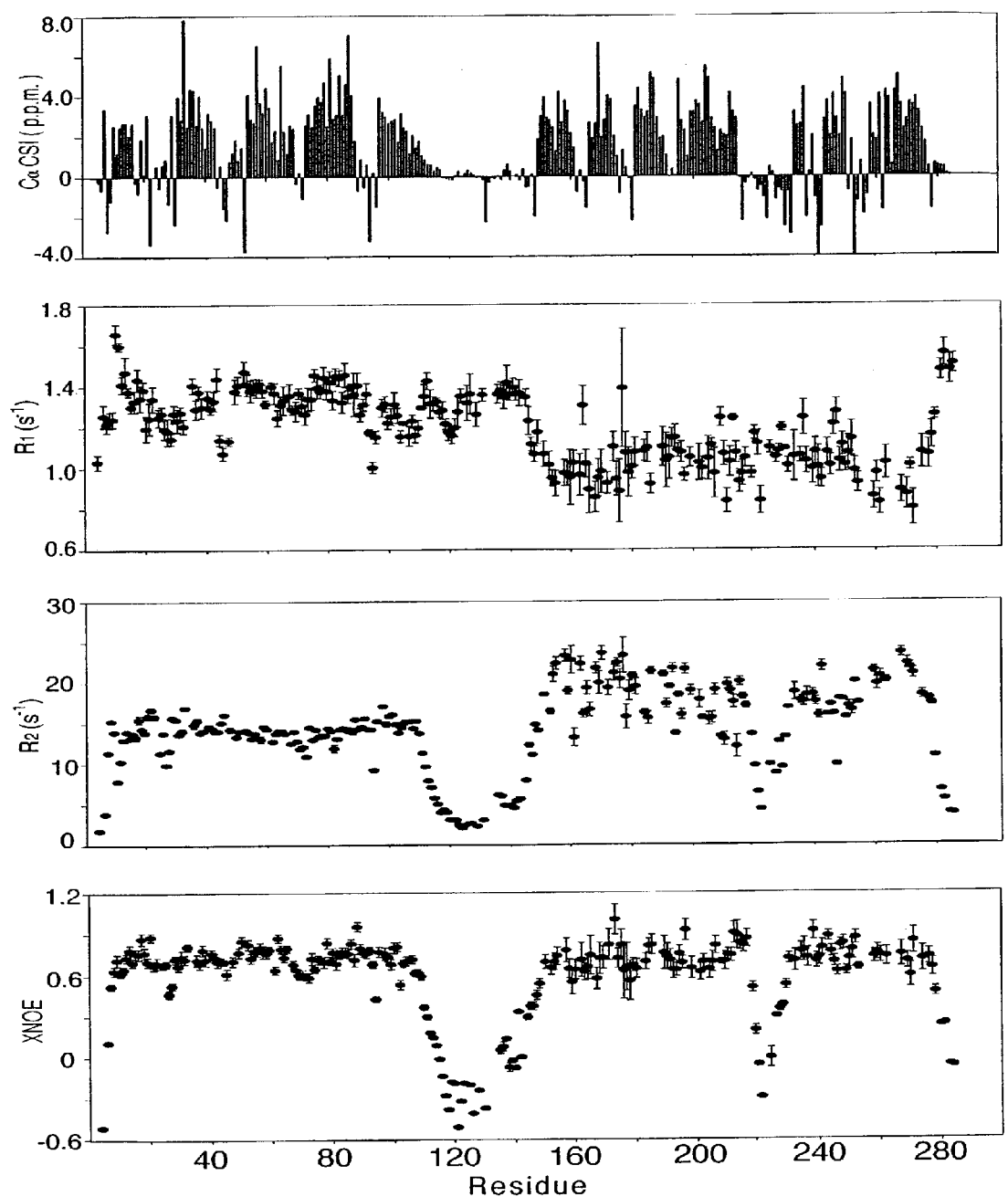
FIG. 6 is a representation of NMR relaxation and chemical shift data that identifies regions of structure and mobility.

Finally, signal doubling and $R_2$ exchange broadening was observed for the backbone amides of Glu 177 and Gly 178 (FIGS. 5 and 6). There are no bulky aromatic side chains in the vicinity of these residues that might cause these effects. Instead, the signal doubling was due to heterogeneity in the Ψ and Φ torsion angles associated with the Glu 177-Gly 178-Ala 179 peptide bonds. Signal doubling was not observed for these residues in the mature protein in which the carbonyl of Gly 178 forms a hydrogen bond with the Ile 134 backbone NH of the β-hairpin.

EXAMPLE 4

Identification of a Ligand Binding Site of the N-Terminal Domain of CA

DNA encoding the CA N-terminal domain (residues 1-151) was amplified from HIV-1 cDNA plasmid pNL-4-3 and an oligonucleotide encoding a C-terminal hexahistidine tag was appended to the gene. The DNA was inserted into a p11a expression vector (Novagen, Madison, Wis.), and the protein product was purified by cobalt affinity chromatography (Clontech, Palo Alto, Calif.); $MW_{calc}$=17523.0 daltons, $MW_{obs}$=17523.10±0.44 daltons (electrospray Mass Spectrometry). The plasmid for the full length, native capsid protein was kindly provided by Dr. W. I. Sundquist (University of Utah, Salt Lake City, Utah), and the protein was purified as described. NMR spectra were assigned using conventional triple resonance methods. Binding isotherms from $^1H$-$^{15}N$ NMR HSQC titration experiments were calculated with ORIGIN 7.0 software (MicroCal, Northampton, Mass.).

To identify compounds that inhibit functions of the capsid protein, public domain chemical libraries were screened for compounds that might bind to clefts on the surface of the capsid protein and tested for binding using NMR titration spectroscopy. Screening efforts focused mainly on a β-hairpin cleft that is exposed on the surface of the N-terminal domain of the immature capsid protein but becomes occupied by residues of a β-hairpin that forms after proteolytic cleavage of Gag. Compounds from public domain chemical libraries were screened using DOCK-4.0, and 40 compounds with good theoretical binding properties (binding energy <−26 kCal/mol, Contact Score <−40) were experimentally tested for binding to the intact CA protein, the N-terminal domain of CA, and a 283 residue fragment of the immature Gag polyprotein (Gag$^{283}$). Several compounds that bind to the capsid protein at a site that appears to be important for capsid assembly were identified. Exemplary compounds include, but are not limited to, N-(3-chloro-4-methylphenyl)-N'-[2-thioethyl-2'-[5-(dimethylaminomethyl)]-2-methylfuryl]urea (CAP-1), N-(4-N-acetamidophenyl)-N'-(3-nitro-4-methyl phenyl) urea (CAP-2), N-(2-propyl)-N'-(3-nitro-4-methyl phenyl) urea (CAP-3), N-(3-chloro-4-methyl phenyl)-N'-(4-cyanophenyl) urea (CAP-4), N-(3-chloro-4-methyl phenyl)-N'-[4-(1,1,1-trichloromethyl)phenyl] urea (CAP-5), N-(3-nitro-4-fluorophenyl)-N'-[3-(1,1,1-trifluoromethyl)phenyl] urea (CAP-6), N-[(3-chloro-4-methyl phenyl)-N',N'-propyl] urea (CAP-7). One compound, N-(3-chloro-4-methylphenyl)-N'-[2-thioethyl-2'-[5-(dimethylaminomethyl)]-2-methylfuryl]urea (CAP-1) was particularly well-tolerated in cell cultures enabling the in vivo antiviral and mechanistic studies described below.

Figure 12:
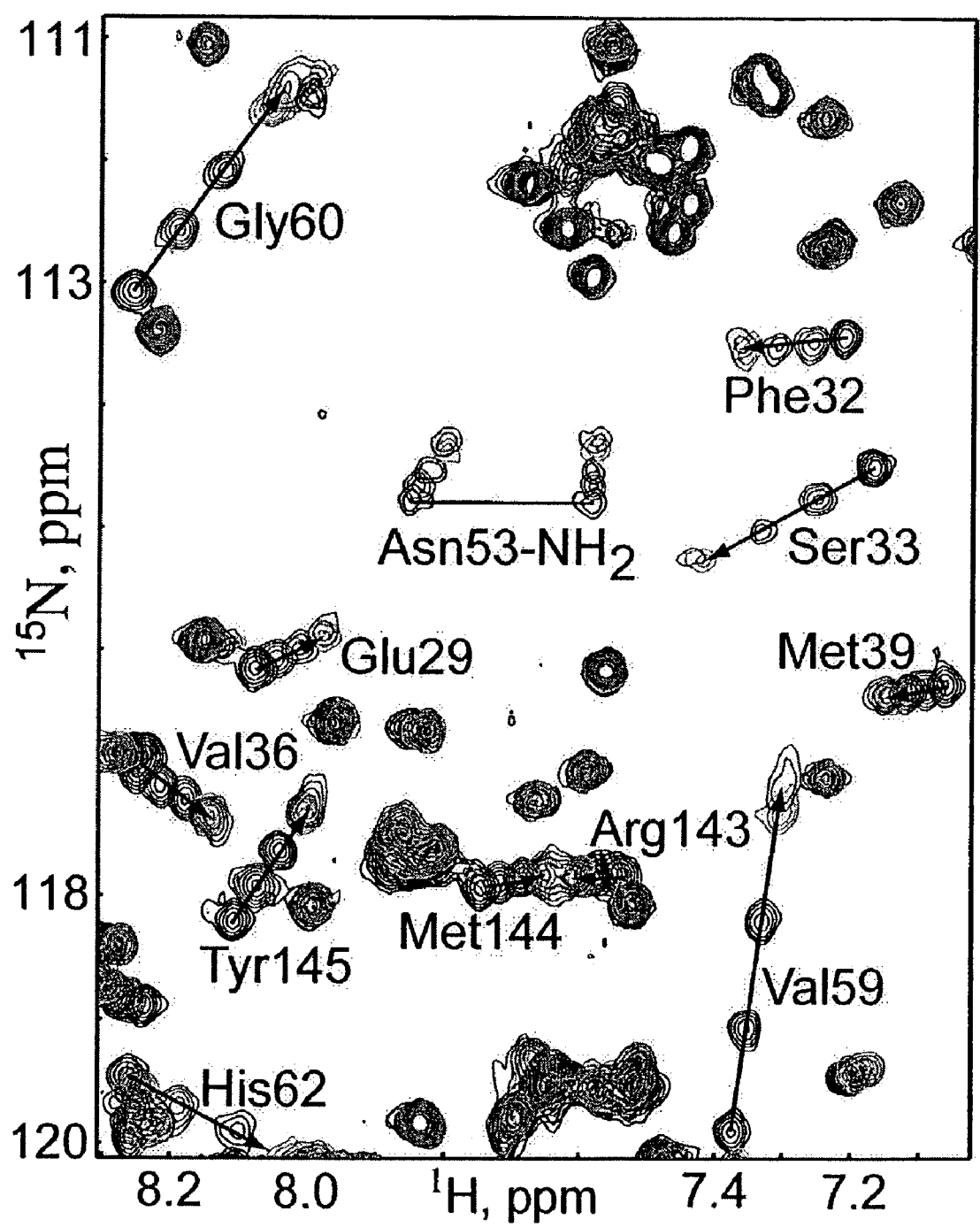
FIG. 12 is a representation of an overlay of 2D $^1H$-$^{15}N$ HSQC spectra obtained for the HIV-1 capsid protein N-terminal domain upon titration with CAP-1.

The mature N-terminal domain was titrated with N-(3-chloro-4-methylphenyl)-N'-[2-thioethyl-2'-[5-(dimethylaminomethyl)]-2-methylfuryl ]urea (CAP-1). Representative $^1H$-$^{15}N$ HSQC NMR data obtained upon titration of the mature NTD with CAP-1 is shown in FIG. 12. Although most signals were unaffected by the titrations, a subset of signals shifted as a function of increasing CAP-1 concentration, indicating site-specific binding.

Similarly, other compounds that bind to the apical cleft of the N-terminal domain of the HIV-1 capsid protein were titrated. In FIG. 13, the superposition of $^1H$-$^{15}N$ HSQC NMR data obtained upon titration of compounds CAP-1, CAP-2, CAP-3, and CAP-4 with the HIV-1 capsid NTD is provided. Compounds CAP-1 and CAP-2 bind to the apical site of the protein, as evidenced by specific chemical shift changes as a function of added compound. Slight perturbations and signal broadening observed upon addition of CAP-3 and CAP-4 indicate very weak binding. In FIG. 14, the superposition of $^1H$-$^{15}N$ HSQC NMR data obtained in the presence and absence of capsid binding compounds CAP-5, CAP-6, and CAP-7 with the HIV-1 capsid NTD is provided. Signals perturbed by binding are shown in circles. For comparison, results obtained with two structurally related compounds that do not bind to the capsid protein are also shown in FIG. 14.

Figure 15:
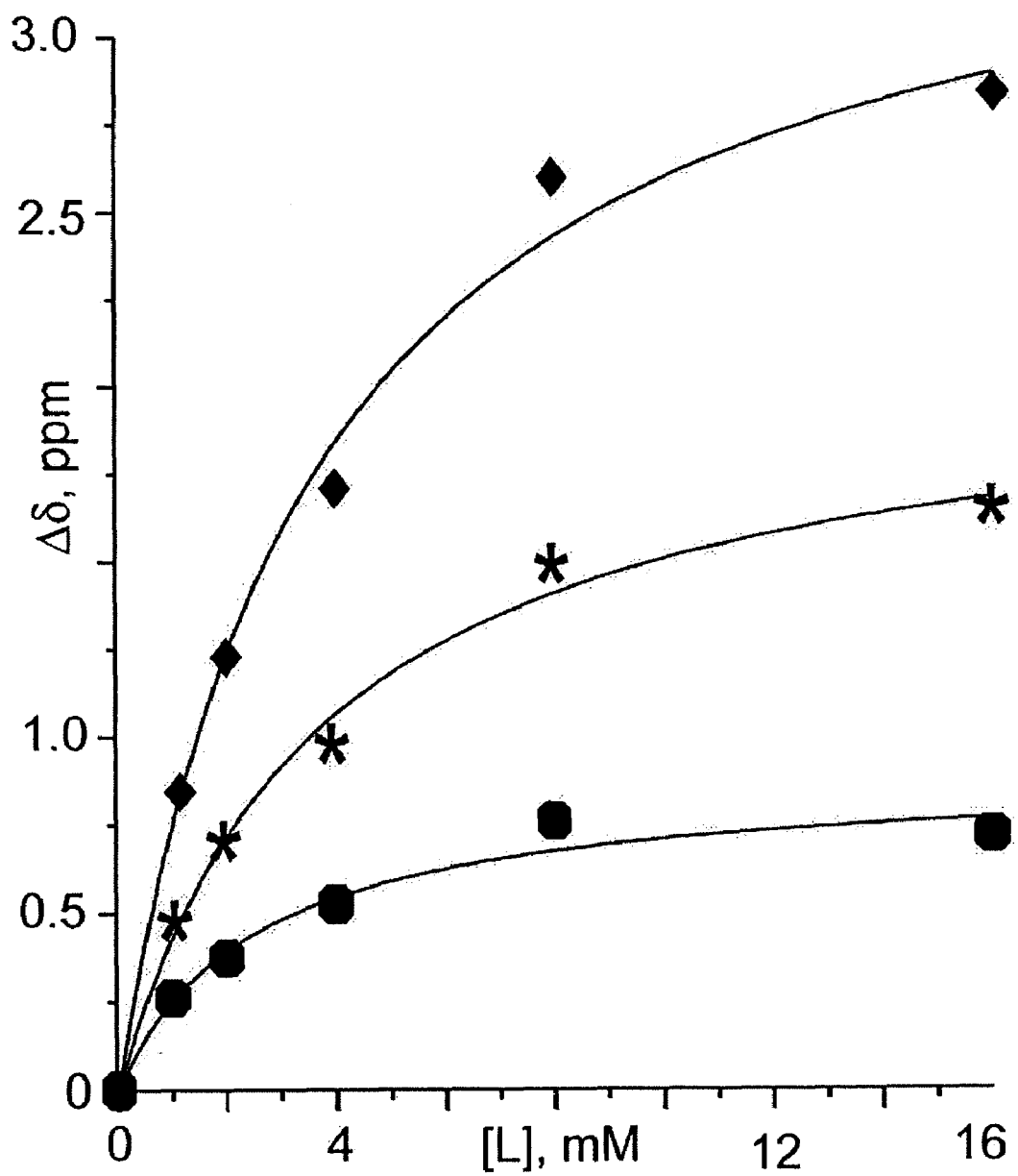
FIG. 15 is a representation of $^{15}N$ NMR chemical shift titration data for residues Ser 33 (squares), Val 59 (diamonds) and Gly 60 (stars) and fit to 1:1 binding isotherms ($K_d$=0.82±0.18 mM).

The chemical shift changes fit to 1:1 binding isotherms and afforded an equilibrium dissociation constant ($K_d$) of 0182±0.18 mM at 35° C. (FIG. 15). Significantly tighter binding was observed for a second compound, 1-(4-(N-methyl-acetamido)phenyl)-3-(4-methyl-3-nitrophenyl)urea (CAP-2), $K_d$=52±27 µM. In both cases, the CA residues perturbed by binding ($^1H_N\Delta\delta$>0.1 ppm; $^{15}N$ Aδ>0.5 ppm; Glu29, Lys30, Ala31, Phe32, Ser33, Glu35, Val36, Val59, Gly60, Gly61, His62, Gln63, Ala65, Met144 and Tyr145) are located at or near the apex of a helical bundle (helices 1, 2, 3, 4 and 7). Essentially identical results were obtained for titrations with Gag$^{283}$ and intact CA, indicating that the binding site remains accessible in Gag-like constructs containing the native N-terminal matrix (MA) and C-terminal capsid (CTD) domains, and that binding is insensitive to the maturation state of the protein.

EXAMPLE 5

In Vitro Inhibition of Capsid Assembly

Turbidity assays were performed at 21° C. using a Beckman DU650 spectrophotometer operating at 350 nm wavelength. Concentrated ligand in DMSO (0.2 µl) was added to a 250 µl aqueous solution containing the capsid protein ([CA]=60 µM; [NaH$_2$PO$_4$]=50 mM; pH 8.0). Particulates were removed by centrifugation, and capsid assembly was initiated by addition of a concentrated NaCl solution (5 M, 250 µl). Spectral measurements were made every 10 s, following a short initial delay to allow sample equilibration.

Relative assembly rates were estimated from initial slopes of the plots of absorbance vs. time.

Figure 16:
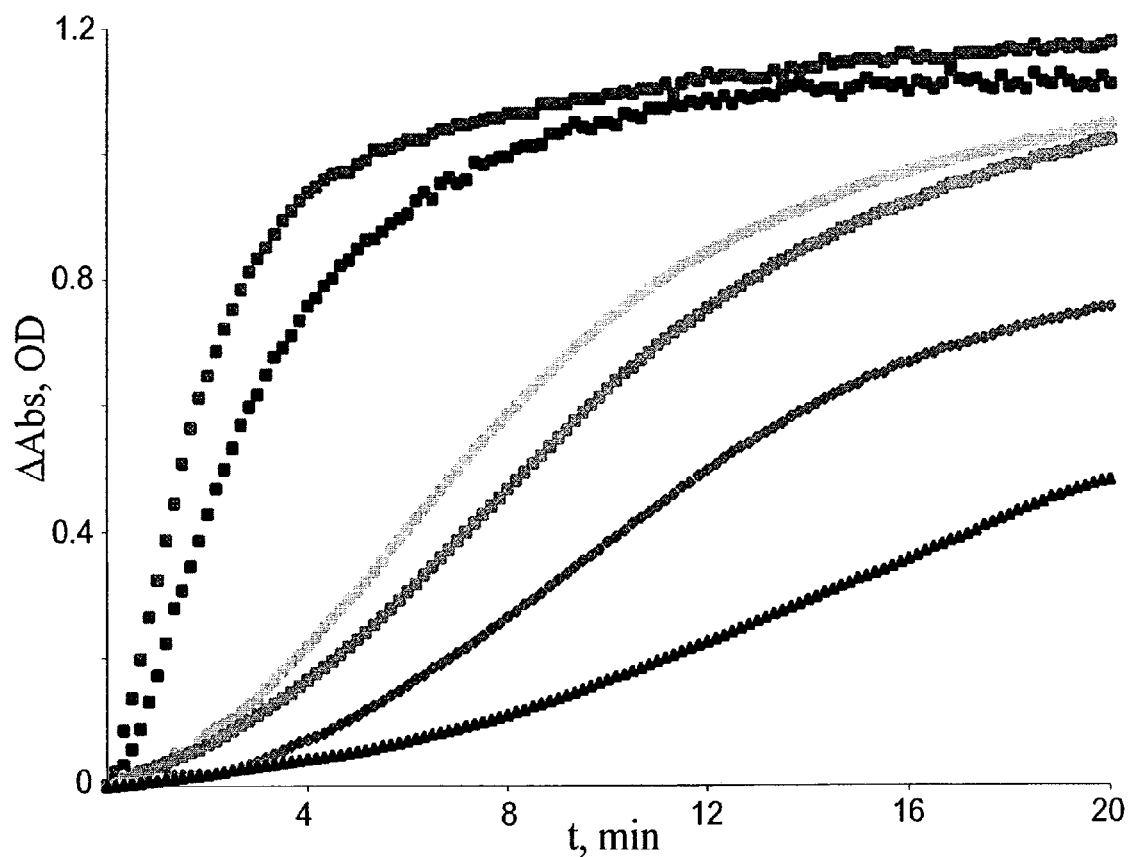
FIG. 16 is a graphical representation of turbidity assay results showing the effects of CA-binding compounds on in vitro capsid assembly.
Figure 17:
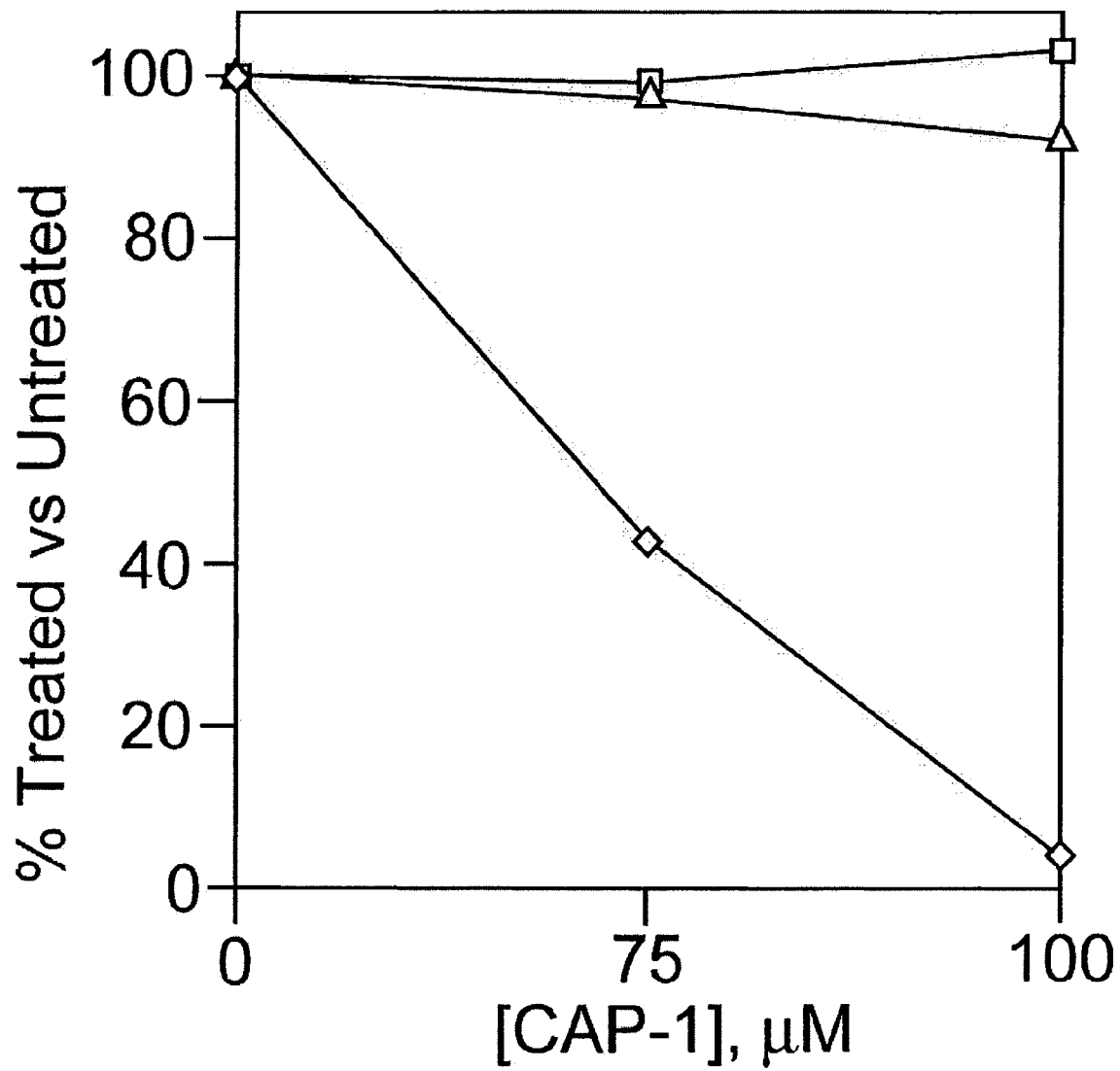
FIG. 17 is a graphical representation of viral infectivity (diamonds), cell viability (squares) and virus production (triangles) from latent infected U1 cultures as a function of added CAP-1.

In the absence of other viral constituents, HIV-1 CA can assemble into tubes with structural features that resemble mature cores. Tube formation leads to increases in sample turbidity that can be monitored spectrophotometrically, and this assay was used to probe for potential inhibitory effects of the CAP compounds on in vitro capsid assembly. As shown in FIG. 17, dissolution of native HIV-1 CA into assembly buffer (50 mM phosphate buffer, pH 8.0, 2.5 M NaCl, 0.04% v/v DMSO) led to an increase in absorbance at an initial rate of 204±36 mOD/min (determined from the initial slope and reported as the mean ± standard deviation from three experiments). As expected, compounds tested that do not bind CA did not affect the rate of assembly. However, the assembly rate was diminished in a dose-dependent manner by both CAP-1 and CAP-2, with the more tightly binding CAP-2 having a more pronounced effect. As shown in FIG. 16, the initial assembly rates in the presence of CAP-1 decreased to 93±3 and 67±16 mOD/min at CAP-1:CA ratios of 1:1 and 2:1, respectively. For comparison, assembly rates in the presence of the more tightly binding CAP-2 decreased to 81±2 and 39±11 mOD/min at CAP-2:CA ratios of 0.5:1 and 1:1, respectively. These data confirm that CA-binding compounds can inhibit capsid assembly in vitro, and that the relative efficacy of assembly inhibition is dependent on the affinity of the ligands for the CA protein.

EXAMPLE 6

Inhibition of Viral Infectivity

U1 cells (5×10$^5$ cells/ml) were mixed with TNF-α (10 ng/ml, Sigma) for activation of HIV virion production and treated with CAP-1 at different concentrations. Cultures were harvested 72 hours after treatment. Cell viability was measured using the MTS cell proliferation assay (CellTiter 96 Aqueous One Solution Cell Proliferation Assay, Promega, Madison, Wis.). Supernatants were collected, the cell debris removed by low speed centrifugation, and the particles in the supernatants pelleted by microcentrifugation. Infectious units associated with the particles were measured as described in Kimpton, et al., Detection of replication-competent and pseudotyped HIV with a sensitive cell line on the basis of activation of an integrated β-galactosidase gene, J. Virol. 66: 2232-39, 1992, except that β-gal activities were measured using a Tropix Gal-Screen detector system (Applied Biosystems, Foster City, Calif.). Particle-associated RT activities were determined as described in Huang, et al., p6Gag is required for particle production from full length human immunodeficiency virus type 1 molecular clones expressing protease, J. Virol., 96: 6810-18, 1995. Cell lysates and pelleted particles were subjected to SDS-PAGE analysis using AIDS patient sera (AIDS Research and Reference Regent Program, NIAID, NIH). Quantitative p24 (CA) assays were performed with the HIV-1 p24 Antigen Capture ELISA kit (AIDS vaccine program, FCRDC/SAIC/NCI, Frederick, Md.). MAGI cells were washed after viral adsorption (HIV-1$_{RF}$) with PBS and were fed fresh media containing CAP-1 at various concentrations. 72 hours post-infection, the culture supernatants were harvested and pre-cleared. Virus particles present on the supernatants were collected by microcentrifugation and particle-associated RT activity and infectivity were subsequently measured.

The CAP compounds were tested for toxicity and antiviral activity using HIV-1 producing, latent infected U1 cells. This assay allows assessment of antiviral effects on late phase replication events. Although CAP-2 was too cytotoxic for in vivo evaluations, CAP-1 was non-toxic under the conditions employed, and its application led to dose dependent reductions in supernatant infectivity, FIG. 17. At 100 μM CAP-1, the U1 cells were fully viable, but infectivity was reduced by ca. 95% relative to untreated samples, FIGS. 18 and 19.

Figure 18:
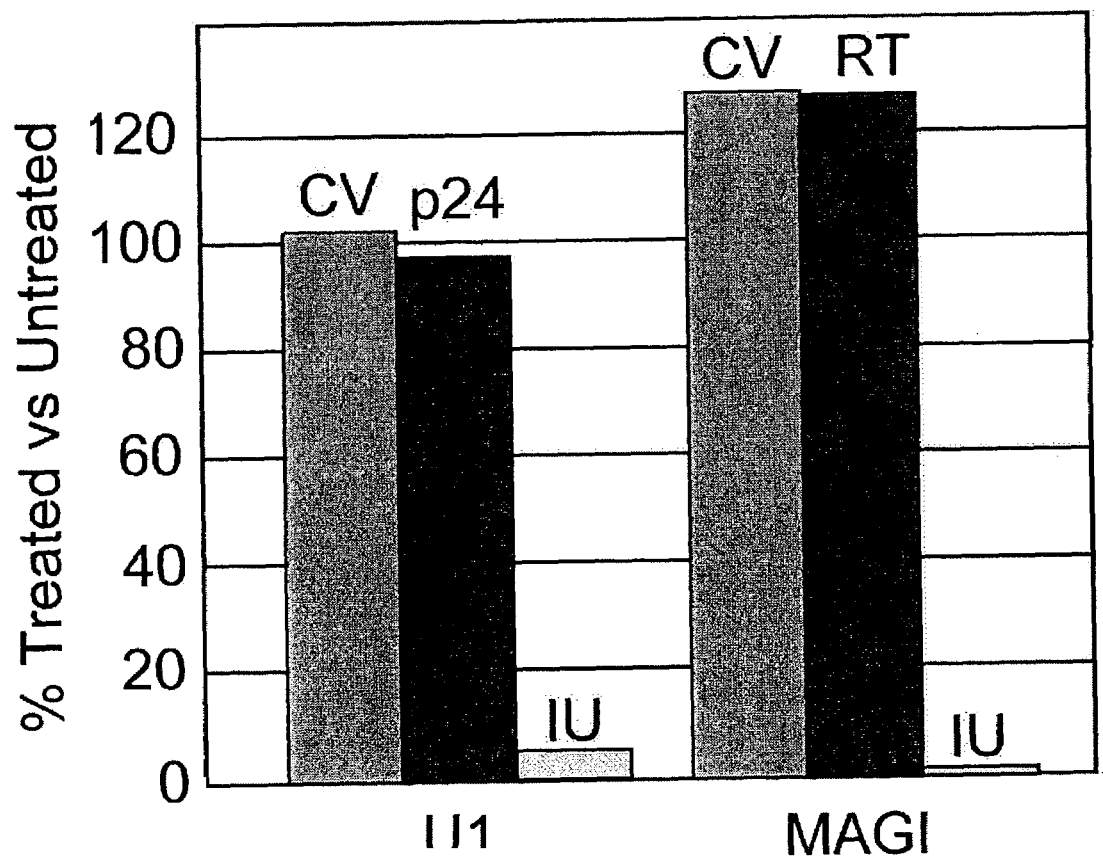
FIG. 18 is a graphical representation of cell viability, virus particle associated RT and CA levels and infectious units obtained upon incubation of infected U1 and MAGI cells for 72 hours with 100 μM CAP-1.
Figure 19:
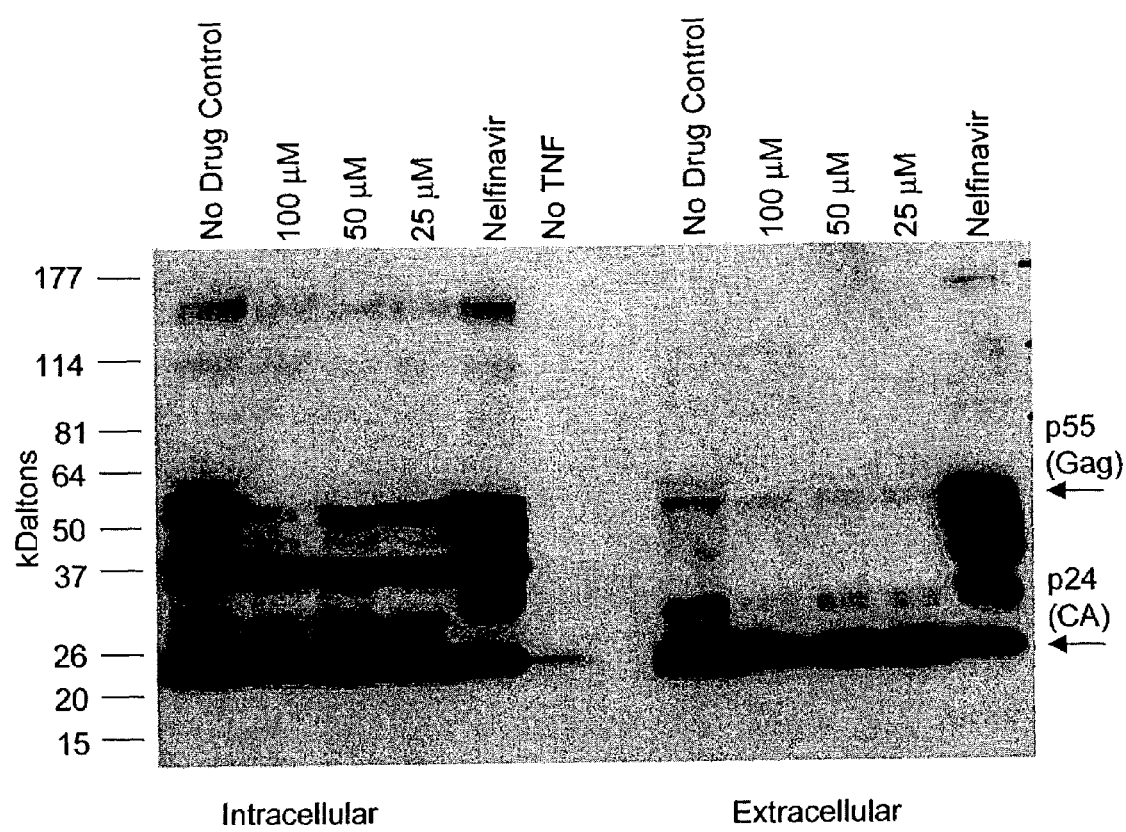
FIG. 19 is a representation of capsid protein Western blot assays showing relative concentrations of intra- and extracellular viral CA in the free, Gag polyprotein and partially processed states as a function of added CAP-1.

To determine if CAP-1 affects viral gene expression and particle production, reverse transcriptase (RT) activity and CA (p24) levels were measured for the supernatants after pelleting and removal of the cells. As shown in FIG. 18, both the CA levels and RT activities were unaffected by CAP-1, indicating that antiviral activity is not due to inhibited virus production. In addition, the p24 (CA) levels observed in Western data obtained for treated and untreated samples were very similar, FIG. 19, indicating that CAP-1 does not significantly affect proteolytic processing of Gag. Consistent with this finding, CAP-1 did not affect in vitro protease activity. The p24 Western data also indicated a reduction in the intracellular levels of Gag (p55) as a function of increasing levels of CAP-1, whereas the levels of the Gag cleavage products p24 and p41 remained relatively unaffected. These findings demonstrate that CAP-1 promotes the intracellular degradation of the full length Gag polyprotein. Quantitation of gp120 was also obtained for the supernatant using antibodies against gp120. No differences were observed between the treated and untreated samples, indicating that CAP-1 does not inhibit the synthesis or viral incorporation of the envelope glycoprotein.

Antiviral activity was also tested in a second cellular assay using MAGI cell cultures. As observed in the U1 assay, treatment of infected, virus producing MAGI cells with CAP-1 led to dose dependent reductions in virus particle infectivity, with infectious units dropping by nearly two log units to less than 2% of the untreated levels at 100 μM CAP-1, FIG. 18. No reductions in viral RT activity were observed, providing further evidence that antiviral activity is not due to inhibited virus production. Virus production was also unaffected by pre-incubation of either MAGI cells or virus particles with CAP-1, indicating that CAP-1 is not virucidal and does not directly inhibit early phase events. These data collectively indicate that the antiviral activity of CAP-1 is due to the inhibition of a late phase viral event that is different from events targeted by other anti-HIV agents currently under investigation or in clinical use.

EXAMPLE 7

In vivo Inhibition of Capsid Assembly

Treated (CAP-1) and untreated virus-producing U1 cells were pelleted, washed in phosphate-buffered saline (PBS) and resuspended in at least ten cell pellet volumes of fixative (100 mM sodium cacodylate, pH 7.2, 2.5% glutaraldehyde, 1.6% paraformaldehyde, 0.5% picric acid). Cells were fixed for 24-48 hours, after which fixative was removed and cells were washed twice in PBS and pelleted in eppendorf centrifuge tubes. Washed cell pellets were post-fixed one hour in 1% osmium tetroxide plus 0.8% potassium ferricyanide in 100 mM sodium cacodylate, pH 7.2. After thorough rinsing in water, cells were pre-stained in 4% uranyl acetate one hour, thoroughly rinsed, dehydrated, infiltrated overnight in 1:1 acetone:Epon 812, infiltrated one hour with 100% Epon 812 resin, and embedded in the resin. After polymerization, 60-80 nm thin sections were cut on a Reichert untramicrotome, stained 5 minutes in lead citrate, rinsed, post-stained 30 minutes in uranyl acetate, rinsed and dried. EM was performed at 60 kV on a Philips CM120/Biotwin equipped with a 1024×1024 Gatan multiscan CCD, and images were collected at original magnifications of 25,880×-36,960×, corresponding t resolutions of 8.9 and 6.5 Å/pixel, respectively. For each sample, 4 separate EM grids were viewed, and at least 47 were collected, corresponding to a minimum total area of 35 micron$^2$.

Since CAP-1 did not inhibit virus production, it was possible to examine the virons produced form treated cells for morphological defects by EM. The capsids of mature virions generally appear as central, conical (approximately 30% of the particles) or spherical (approximately 40%) structures, depending on the orientation of the cone during thin section sample preparation, and about 30% of virions in EM preparations typically exhibit an immature phenotype characterized by the lack of central electron density. Virions from untreated U1 cell cultures generated these typical results. However, particles generated from the treated cells exhibited greater size heterogeneity, which is indicative of a Gag assembly defect. In addition, only 35% of the particles from the treated cells contained a dense, centrally located core, compared to 70% from the untreated cells. Most strikingly, none of the particles from the treated cells exhibited a cone-shaped core that is the hallmark of HIV, indicating that CAP-1 inhibits assembly of the mature core. Essentially identical phenotypes were observed previously for virions generated with CA mutations designed to disrupt intermolecular CA-CA interactions. Thus, this EM data indicates that CAP-1 inhibits capsid assembly during viral maturation and interferes to some extent with normal Gag-Gag interactions during assembly of the immature particle.

Numerous modifications and variations of the above-described invention are expected to occur to those of skill in the art. Accordingly, only such limitations as appear in the appended claims should be placed thereon.

What is claimed is:

1. A method of evaluating the antiviral activity of a test compound comprising:
    a) contacting said test compound with Gag$^{283}$ or a fragment of Gag$^{283}$ that promotes assembly of the viral capsid,
    b) determining an ability of said test compound contacted with Gag$^{283}$ or said fragment of Gag$^{283}$ to bind to the apical cleft near the C-terminal end of the N-terminal domain of a capsid protein of HIV-1 or HIV-2, and
    c) evaluating an antiviral effect of said compound, which binds to said apical cleft.

2. The method of claim 1 wherein the capsid protein is an HIV-1 capsid protein.

3. The method of claim 1 wherein the HIV capsid protein is mature.

4. The method of claim 1 wherein the HIV capsid protein is immature.

5. The method of claim 2 wherein the HIV capsid protein is mature.

6. The method of claim 2 wherein the HIV capsid protein is immature.

7. The method of claim 1 wherein the antiviral activity is selected from the group consisting of inhibition of capsid assembly during viral maturation and inhibition of disassembly during infectivity.

* * * * *